United States Patent
Bacquéet al.

(10) Patent No.: US 6,841,562 B2
(45) Date of Patent: Jan. 11, 2005

(54) QUINOLYLPROPYLPIPERIDINE DERIVATIVES, INTERMEDIATES AND COMPOSITIONS CONTAINING THEM, AND PREPARATION THEREFOR

(75) Inventors: Eric Bacqué, Gif sur Yvette (FR); Antony Bigot, Massy (FR); Youssef El Ahmad, Créteil (FR); Jean-Luc Malleron, Marcoussis (FR); Serge Mignani, Chatenay Malabry (FR); Baptiste Ronan, Clamart (FR); Michel Tabart, La Norville (FR); Fabrice Viviani, Louvres (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 10/659,095

(22) Filed: Sep. 10, 2003

(65) Prior Publication Data

US 2004/0082610 A1 Apr. 29, 2004

(30) Foreign Application Priority Data

Sep. 11, 2002 (FR) ............................................. 02 11213

(51) Int. Cl.⁷ ..................... A61K 31/44; C07D 215/12; C07D 215/18
(52) U.S. Cl. ........................ 514/314; 546/177; 546/176
(58) Field of Search .......................... 514/314; 546/177, 546/176

(56) References Cited

U.S. PATENT DOCUMENTS

| 5,296,484 | A | * | 3/1994 | Coghlan et al. | ............ 514/311 |
| 6,117,884 | A | * | 9/2000 | Daeuble et al. | ............ 514/311 |
| 6,603,005 | B2 | * | 8/2003 | Baque et al. | ................ 546/176 |

FOREIGN PATENT DOCUMENTS

| WO | WO 00/43383 | 7/2000 |
| WO | WO 01/25227 | 4/2001 |
| WO | WO 02/40474 | 5/2002 |

* cited by examiner

Primary Examiner—D. Margaret Seaman
(74) Attorney, Agent, or Firm—Balaram Gupta

(57) ABSTRACT

Quinolylpropylpiperidine derivatives of general formula (I) in which $R_{1a}$ is hydrogen, halogen, hydroxyl, amino, alkylamino, dialkylamino, hydroxyamino, alkoxyamino or alkylalkoxyamino and $R_{1b}$ is hydrogen, or $R_{1a}$ and $R_{1b}$ form an oxo, $R_2$ is carboxyl, carboxymethyl or hydroxymethyl, $R_3$ is alkyl either substituted with phenylthio optionally substituted with halogen, hydroxyl, alkyl, alkoxy, trifluoromethyl, trifluoromethoxy, carboxyl, alkoxycarbonyl, cyano or amino, or with cycloalkylthio (3 to 7 members) optionally substituted with halogen or trifluoromethyl, or with heteroarylthio (5 to 6 members and 1 to 4 heteroatoms chosen from N, O and S), optionally substituted with halogen, hydroxyl, alkyl, alkoxy, trifluoromethyl, trifluoromethoxy, carboxyl, alkoxycarbonyl, cyano or amino or $R_3$ is propargyl substituted with phenyl or heteroaryl as defined above, $R_4$ is alkyl, alkenyl-$CH_2$— or alkynyl-$CH_2$—, cycloalkyl or cycloalkylalkyl, in their various isomeric forms, separate or as mixtures, and also their salts, their preparation process and intermediates and the compositions containing them. These novel derivatives are potent antibacterial agents.

(I)

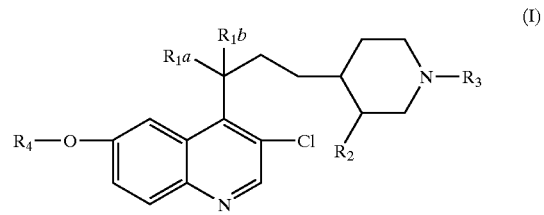

27 Claims, No Drawings

QUINOLYLPROPYLPIPERIDINE DERIVATIVES, INTERMEDIATES AND COMPOSITIONS CONTAINING THEM, AND PREPARATION THEREFOR

This application claims the benefit of priority of French Patent Application No. 02/11,213, filed Sep. 11, 2002.

The present invention relates to quinolylpropylpiperidine derivatives of general formula (I):

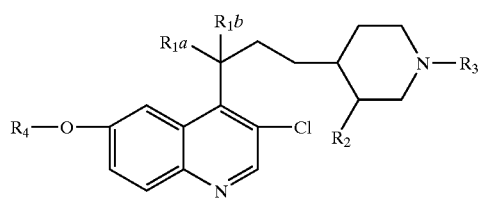

(I)

which are active as antimicrobials. The invention also relates to their preparation process and intermediates and to pharmaceutical compositions containing them.

In Patent Applications WO 99/37635 and WO 00/43383, there have been described antimicrobial quinolylpropylpiperidine derivatives of general formula:

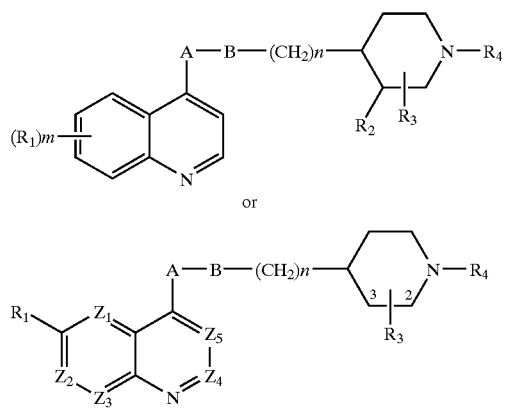

in which the radical $R_1$ is in particular (C1–6)alkoxy, $R_2$ is hydrogen, $R_3$ is at the 2- or 3-position and represents (C1–6)alkyl which may be optionally substituted with 1 to 3 substituents chosen from thiol, halogen, alkylthio, trifluoromethyl, carboxyl, alkoxycarbonyl, alkylcarbonyl, alkenyloxycarbonyl, alkenylcarbonyl, hydroxyl optionally substituted with alkyl, and the like, $R_4$ is a group —$CH_2$—$R_5$ for which $R_5$ is selected from alkyl, hydroxyalkyl, alkenyl, alkynyl, tetrahydrofuryl, phenylalkyl which is optionally substituted, phenylalkenyl which is optionally substituted, heteroarylalkyl which is optionally substituted, heteroaryl which is optionally substituted, and the like, n is 0 to 2, m is 1 or 2 and A and B are in particular oxygen, sulfur, sulfinyl, sulfonyl, $NR_{11}$, $CR_6R_7$ for which $R_6$ and $R_7$ represent H, thiol, alkylthio, halo, trifluoromethyl, alkenyl, alkenylcarbonyl, hydroxyl, amino, and $Z_1$ to $Z_5$ are N or $CR_{1a}$, and the like.

In European Patent Application EP30044, there have been described quinoline derivatives which are useful as cardiovascular agents and which correspond to the general formula:

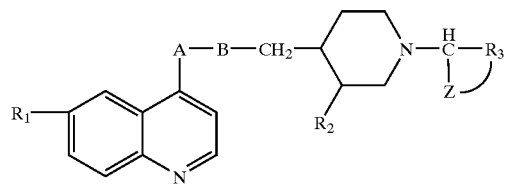

in which $R_1$ is in particular alkoxy, A—B is —$CH_2$—$CH_2$—, —CHOH—$CH_2$—, —$CH_2$—CHOH—, —$CH_2$—CO— or —CO—$CH_2$—, $R_1$ is H, OH or alkoxy, $R_2$ is ethyl or vinyl, $R_3$ is in particular alkyl, hydroxyalkyl, cycloalkyl, hydroxyl, alkenyl, alkynyl, tetrahydrofuryl, phenylalkyl, diphenylalkyl which is optionally substituted, phenylalkenyl which is optionally substituted, benzoyl or benzoylalkyl which is optionally substituted, heteroaryl or heteroarylalkyl which is optionally substituted and Z is H or alkyl or forms with $R_3$ a cycloalkyl radical.

It has now been found, and this is what constitutes the subject of the present invention, that the products of general formula (I) for which:

$R_{1a}$ is hydrogen or a halogen atom or a hydroxyl, amino, alkylamino, dialkylamino, hydroxyamino, alkoxyamino or alkylalkoxyamino radical, and $R_{1b}$ is a hydrogen atom, or $R_{1a}$ and $R_{1b}$ form an oxo group, $R_2$ represents a carboxyl, carboxymethyl or hydroxymethyl radical, $R_3$ represents an alkyl (1 to 6 carbon atoms) radical substituted with a phenylthio radical which may itself carry 1 to 4 substituents chosen from the group consisting of halogen, hydroxyl, alkyl, alkoxy, trifluoromethyl, trifluoro-methoxy, carboxyl, alkoxycarbonyl, cyano and amino, with a cycloalkylthio radical in which the cyclic portion contains 3 to 7 members, which may itself carry one or more substituents chosen from halogen and trifluoromethyl, or with a 5- to 6-membered heteroarylthio radical comprising 1 to 4 heteroatoms chosen from nitrogen, oxygen and sulfur, which may itself carry one or more substituents chosen from the group consisting of halogen, hydroxyl, alkyl, alkoxy, trifluoromethyl, trifluoro-methoxy, carboxyl, alkoxycarbonyl, cyano and amino or $R_3$ represents a propargyl radical substituted with a phenyl radical which may itself carry 1 to 4 substituents chosen from the group consisting of halogen, hydroxyl, alkyl, alkoxy, trifluoromethyl, trifluoromethoxy, carboxyl, alkoxycarbonyl, cyano and amino, or substituted with a 3- to 7-membered cycloalkyl radical which may itself carry one or more substituents chosen from halogen and trifluoromethyl, or substituted with a 5- to 6-membered heteroaryl radical comprising 1 to 4 heteroatoms chosen from nitrogen, oxygen and sulfur, which may itself carry one or more substituents chosen from the group consisting of halogen, hydroxyl, alkyl, alkoxy, trifluoromethyl, trifluoromethoxy, carboxyl, alkoxycarbonyl, cyano and amino, and $R_4$ represents an alkyl radical containing 1 to 6 carbon atoms, an alkenyl-$CH_2$— or alkynyl-$CH_2$— radical in which the alkenyl or alkynyl portions contain 2 to 6 carbon atoms, a cycloalkyl or cycloalkylalkyl radical in which the cycloalkyl portion contains 3 to 8 carbon atoms, in their isomeric, enantiomeric and diastereoisomeric forms, separate or as mixtures, and also their salts, are potent antibacterial agents.

It is understood that the alkyl radicals and portions are in the form of a straight or branched chain and contain (unless otherwise stated) 1 to 4 carbon atoms, and that in the alternative case where $R_1$ represents a halogen atom or when $R_3$ carries a halogen substituent, the latter may be chosen from fluorine, chlorine, bromine and iodine, fluorine being preferred.

In the above general formula, when $R_3$ carries a heteroaryl substituent, the latter may be chosen, without limitation, from thienyl, furyl, pyrrolyl, imidazolyl, thiazolyl, oxazolyl, thiadiazolyl, oxadiazolyl, tetrazolyl, pyridyl, pyridazinyl, pyrazinyl and pyrimidinyl.

A subject of the invention is in particular the derivatives of general formula (I) as defined above, in which $R_{1a}$ is a hydroxy radical and $R_{1b}$ is a hydrogen atom, those in which $R_{1a}$ and $R_{1b}$ form an oxo group, those in which $R_4$ represents an alkyl radical containing from 1 to 6 carbon atoms, in particular methyl, those in which $R_2$ represents a carboxyl radical and those in which $R_3$ represents an alkyl radical, in particular ethyl, substituted with a phenylthio, cycloalkylthio or heteroarylthio radical optionally substituted as defined above, more particularly those in which $R_3$ represents an ethyl radical substituted with a thienylthio radical or a phenylthio radical substituted with halogen, in particular fluorine, or with trifluoromethyl, cyclohexylthio or cyclopentylthio.

A subject of the invention is more particularly the derivatives of general formula (I) with the following names:

4-[3-hydroxy-3-(3-chloro-6-methoxyquinoline-4-yl)propyl]-1-[2-(2,5-difluorophenylsulfanyl)ethyl]piperidine-3-carboxylic acid;
4-[3-hydroxy-3-(3-chloro-6-methoxyquinoline-4-yl)propyl]-1-[2-(2-thienylsulfanyl)ethyl]piperidine-3-carboxylic acid;

in their various isomeric forms, separate or as mixtures, and also their salts.

According to the invention, the products of general formula (I) may be obtained by condensing the $R_3$ chain with the quinolylpropylpiperidine derivative of general formula (II):

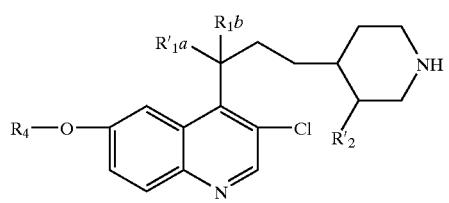

(II)

in which $R_4$ is as defined above, either $R'_{1a}$ represents a hydrogen atom or a hydroxyl radical and $R_{1b}$ represents a hydrogen atom or $R'_{1a}$ and $R_{1b}$ form an oxo group and $R'_2$ represents a protected carboxyl or carboxymethyl radical, to obtain a quinolylpropylpiperidine derivative of general formula (III):

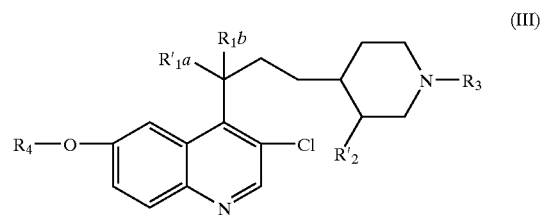

(III)

for which $R'_{1a}$, $R_{1b}$, $R'_2$ and $R_4$ are as defined above and $R_3$ is as defined above, then, where appropriate, halogenation of the derivative for which $R'_{1a}$ is a hydroxyl radical and $R_{1b}$ is a hydrogen atom, if it is desired to obtain a derivative for which $R'_{1a}$ is a halogen atom, or, where appropriate, conversion of the hydroxyl radical represented by $R'_{1a}$ to an oxo radical, and then, where appropriate, conversion thereof to a hydroxyimino or alkoxyimino radical, to obtain a quinolylpropylpiperidine derivative of general formula (IV):

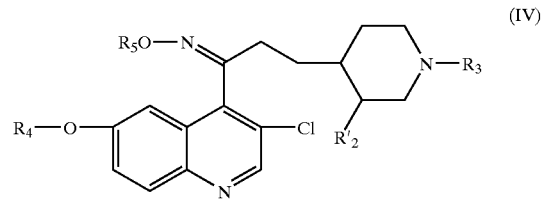

(IV)

for which $R'_2$, $R_3$ and $R_4$ are as defined above, and $R_5$ is a hydrogen atom or an alkyl radical, and reduction of the derivative of general formula (IV) for which $R_5$ is a hydrogen atom to an amine, and optionally conversion to a monoalkylated or dialkylated amine, or optionally reduction of the derivative of general formula (IV) for which $R_5$ is a hydrogen atom to a hydroxylamine or of the derivative of general formula (IV) for which $R_5$ is an alkyl radical to an alkoxyamine, and then, where appropriate, to obtain the derivative for which $R_{1a}$ is alkylalkoxyamino, conversion of the derivative obtained for which $R_{1a}$ is alkoxyamino by alkylation, then conversion of $R'2$ to a carboxyl or carboxymethyl radical, and/or, where appropriate, reduction of the carboxyl radical thus obtained or of the protected carboxyl radical which may be represented by $R'_2$ to a hydroxymethyl radical and, where appropriate, conversion thereof to a carboxymethyl radical according to the usual methods, and then, where appropriate, separation of the isomers, removal, where appropriate, of the acid-protecting radical, and/or, where appropriate, conversion of the product obtained to a salt.

The condensation of the chain $R_3$ with piperidine is advantageously carried out by the action of a derivative of general formula:

$R_3$—X (V)

in which $R_3$ is as defined above and X represents a halogen atom, a methylsulfonyloxy radical, a trifluoromethylsulfonyloxy or p-toluenesulfonyloxy radical, the procedure being carried out in an anhydrous, preferably inert (nitrogen or argon for example) medium, in an organic solvent such as an amide (dimethylformamide for example), a ketone (acetone for example) or a nitrile (acetonitrile for example) in the presence of a base such as a nitrogen-containing organic base (for example triethylamine) or an inorganic base (alkali metal carbonate, potassium carbonate for example) at a temperature in the range of from about 20° C. and the reflux temperature of the solvent. Preferably, a derivative for which X is a bromine or iodine atom is caused to react.

Derivatives of formula (V) are described or can be prepared as described, for example, in applications WO 200125227 or WO 200240474.

When $R_3$ represents propargyl substituted with phenyl, cycloalkyl or heteroaryl, it may also be preferable to condense a propargyl halide, and then to substitute the chain with a phenyl, cycloalkyl or heteroaryl radical. In this alternative case, the condensation of the propargyl chain is carried out by means of propargyl bromide, under the conditions set out above, where appropriate, in the presence of an alkali metal iodide such as for example potassium or sodium iodide.

When substitution with a phenyl or heteroaryl radical is involved, the reaction is carried out by the action of a halide derived from the cyclic radical to be substituted, in the presence of triethylamine, in anhydrous medium, optionally with no solvent or in a solvent such as an amide (dimethylformamide for example) or a nitrile (acetonitrile for example) and in the presence of a palladium salt such as for example tetrakis(triphenylphosphine)palladium and copper(I) iodide, at a temperature in the range of from about 20° C. and the reflux temperature of the solvent.

When substitution with a cycloalkyl group is involved, the reaction is carried out by the action of an organolithium compound such as n-butyllithium or tertbutyllithium on the propargyl derivative obtained above, in anhydrous medium in an ether such as for example tetrahydrofuran at a temperature in the range of from about −78° C. to about 0° C., followed by the action of a cycloalkanone followed by the deoxygenation of the intermediate alcohol according to conventional methods.

It is understood that when the alkyl radicals represented by $R_3$ carry carboxyl or amino substituents, the latter are protected beforehand and then released after the reaction. The procedure is carried out according to customary methods which do not adversely affect the rest of the molecule, in particular according to the methods described by T. W. Greene and P. G. M. Wuts, Protective Groups in Organic Synthesis (2nd ed.), A. Wiley—Interscience Publication (1991), or by Mc Omie, Protective Groups in Organic Chemistry, Plenum Press (1973).

The protected carboxyl or carboxymethyl radical represented by $R'_2$ may be chosen from the easily hydrolyzable esters. By way of example, there may be mentioned methyl, benzyl or tert-butyl esters, or allyl or phenylpropyl esters. Optionally, the carboxyl radical is protected simultaneously with the reaction. In this case, the product of general formula (II) used carries a radical $R'_2$=carboxyl or carboxymethyl.

The halogenation leading to a derivative for which $R_{1a}$ is a halogen atom may be carried out in the presence of an aminosulfur trifluoride (diethylaminosulfur trifluoride, bis (2-methoxyethyl)aminosulfur trifluoride (Deoxofluor®), morpholinosulfur trifluoride for example) or alternatively in the presence of sulfur tetrafluoride. The fluorination reaction may also be carried out by the action of a fluorinating agent such as a sulfur fluoride [for example morpholinosulfur trifluoride, sulfur tetrafluoride (J. Org. Chem., 40, 3808 (1975)), diethylaminosulfur trifluoride (Tetrahedron, 44, 2875 (1988)), bis(2-methoxyethyl)-aminosulfur trifluoride (Deoxofluor®). Alternatively, the fluorination reaction may also be carried out by means of a fluorinating agent such as hexafluoropropyldiethylamine (JP 2 039 546) or N-(2-chloro-1,1,2-trifluoroethyl)diethylamine. The halogenation reaction may also be carried out using a reagent such as tetraalkylammonium, trialkylbenzylammonium or trialkylphenylammonium halide or using an alkali metal halide optionally substituted with a crown ether.

When a tetraalkylammonium halide is used, the latter may be chosen, by way of example, from tetramethylammonium, tetraethylammonium, tetrapropylammonium, tetrabutylammonium (tetra-n-butylammonium for example), tetrapentylammonium, tetracyclohexylammonium, triethylmethylammonium, tributylmethylammonium or trimethylpropylammonium halides.

The procedure is carried out in an organic solvent such as a chlorinated solvent (for example dichloromethane, dichloroethane or chloroform) or in an ether (tetrahydrofuran or dioxane for example) at a temperature in the range of from about −78° C. to about 40° C. (preferably between 0 and 30° C.). It is advantageous to carry out the procedure in an inert medium (argon or nitrogen in particular).

It is also possible to carry out the procedure by the action of a halogenating agent such as thionyl chloride or phosphorus trichloride in an organic solvent such as a chlorinated solvent (dichloromethane or chloroform for example), at a temperature in the range of from about 0° C. and the reflux temperature of the reaction mixture.

The conversion of the hydroxyl radical to an oxo radical is carried out using conventional oxidation methods described in the literature, for example by D. Swern oxidation, J.O.C., 44, 41–48 (1979) in particular in the presence of oxalyl chloride and of dimethyl sulfoxide, optionally in a solvent, for example dichloromethane, at a temperature in the range of from about −60° C. to about 20° C.

The conversion of the oxo radical to a hydroxyimino or alkoxyimino radical is carried out by the action of hydroxylamine or of alkoxyamine, optionally in hydrochloride form, in a solvent such as pyridine or an alcohol (such as methanol or ethanol) and in the presence of a nitrogen base such as triethylamine or pyridine at a temperature in the range of from about 0° C. to about 60° C.

The reduction of the derivative of general formula (IV), for which $R_5$ is hydrogen, to an amine is carried out according to the customary methods which do not adversely affect the rest of the molecule, in particular by the action of a reducing agent such as for example a hydride (alkali metal borohydride: sodium or potassium borohydride for example or aluminum and lithium hydride) in the presence or in the absence of molybdenum oxide, the procedure being preferably carried out under an inert atmosphere (nitrogen or argon for example), in an organic solvent such as an alcohol (methanol, ethanol or isopropanol for example) or a chlorinated solvent (for example dichloromethane) at a temperature in the range of from about −10° C. to about 40° C.

The reduction of the derivative of general formula (IV) to a hydroxylamine or to an alkoxyamine is carried out in particular in the presence of an organic acid (carboxylic acid such as for example acetic acid), by the action of a reducing agent such as for example a hydride chosen from sodium triacetoxy-borohydride (optionally prepared in situ) or sodium cyanoborohydride, preferably under an inert atmosphere (nitrogen or argon for example), in an organic solvent such as an alcohol (methanol, ethanol or isopropanol for example) or a chlorinated solvent (for example dichloromethane) at a temperature in the range of from about −30° C. to about +40° C.

The conversion of the amino radical represented by $R_{1a}$ to an alkylamino or dialkylamino radical is carried out according to the customary methods, in particular by the action of an alkyl halide, optionally in a basic medium in the presence of a nitrogen base such as a trialkylamine (triethylamine, diisopropylethylamine, and the like), pyridine, or in the presence of an alkali metal hydride (sodium hydride), in an inert solvent such as an amide (dimethylformamide for example) or an oxide (dimethyl sulfoxide for example), at a temperature in the range of from about 20° C. and the reflux temperature of the reaction medium.

The conversion of the alkoxyamino radical represented by $R_{1a}$ to an alkylalkoxyamino radical is carried out according to the method described above for the alkylation of the amine.

The conversion of $R'_2$ to a carboxyl or carboxymethyl radical is carried out according to the usual methods, in particular by acid hydrolysis or saponification of the ester $R'_2$. In particular, sodium hydroxide is caused to act in an aqueous-organic medium, for example in an alcohol such as methanol or an ether such as dioxane, at a temperature in the range of from about 20° C. and the reflux temperature of the reaction mixture. It is also possible to use hydrolysis in aqueous hydrochloric medium at a temperature in the range of from about 20° C. to about 100° C.

The reduction to a hydroxymethyl radical of a derivative for which $R'_2$ is a protected carboxyl can be carried out according to the usual methods, known to those skilled in the art, which do not adversely affect the rest of the molecule, in particular by the action of a hydride (aluminum and lithium hydride or diisobutylaluminum hydride for example) in a solvent such as an ether (tetrahydrofuran for example) at a temperature in the range of from about 20° C. to about 60° C.

The reduction of the free acid can be carried out according to methods also known to those skilled in the art, for example by hydrogenation in the presence of a rhodium-based or ruthenium-based catalyst, by the action of sodium hydroboride in the presence of a Lewis acid or of lithium aluminum hydride in ether.

The conversion of the hydroxymethyl radical in the 3-position of the piperidine to a carboxymethyl radical is carried out according to the usual methods which do not adversely effect the rest of the molecule, in particular by the action of a halogenating agent, such as, for example, thionyl chloride or phosphorus trichloride or phosphorus tribromide, or of a tosylating agent, and then of an alkali metal cyanide, for example potassium cyanide or sodium cyanide, to prepare the corresponding cyanomethyl derivative, followed by hydrolysis of the nitrile. When the radical $R_1$ is an amino radical, it is preferable to protect this radical beforehand, according to the known methods mentioned above for $R_3$.

The halogenation can be carried out in a chlorinated solvent (dichloromethane or chloroform for example), at a temperature in the range of from about 0° C. and the reflux temperature of the solvent.

The quinolylpropylpiperidine derivative of general formula (II), for which $R'_{1a}$ is a hydroxyl radical and $R_{1b}$ a hydrogen atom, can be prepared by oxidation in basic medium at the start of a corresponding derivative for which $R'_{1a}$ and $R_{1b}$ are hydrogen atoms, the amino functional group of the piperidine is intermediately protected and $R'_2$ is as defined above or represents a carboxyl or carboxymethyl radical and, where appropriate, reprotection of the carboxyl or carboxymethyl radical. The oxidation is carried out by the action of oxygen, preferably in an inert solvent such as dimethyl sulfoxide in the presence of tertbutanol and of a base such as potassium or sodium tertbutoxide, at a temperature in the range of from about 0° C. to about 100° C.

The quinolylpropylpiperidine derivative of general formula (II) in which $R'_{1a}$ and $R_{1b}$ form an oxo group can be prepared in a similar manner to that indicated above, by conventional oxidation methods, starting with a derivative of general formula (II) in which $R'_{1a}$ represents a hydroxyl radical, intermediately protecting the nitrogen of the piperidine.

The quinolylpropylpiperidine derivative of general formula (II) for which $R'_2$ represents a protected carboxymethyl radical, and $R'_{1a}$ and $R_{1b}$ are hydrogen atoms, may be prepared by selective hydrogenation of the quinolylpropylpiperidine derivative of general formula (VI):

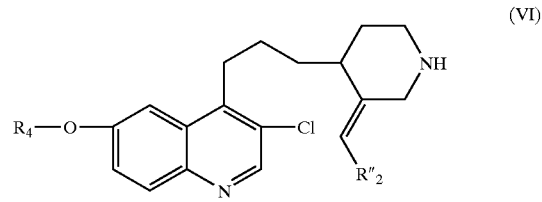

(VI)

in which $R_4$ is as defined above and $R''_2$ is the protected carboxyl radical corresponding to $R'_2$, and in which the amine functional group of the piperidine is protected beforehand, at a pressure of from about 1 to about 100 bar and at a temperature in the range of from about 20° C. to about 80° C., in a solvent such as in particular an alcohol (ethanol for example) or an amide (dimethylformamide for example) in the presence of a catalyst, for example palladium on carbon or palladium on barium sulfate.

The protection of the amino group of the piperidine is carried out according to the customary methods which do not adversely affect the rest of the molecule and which are compatible with the reaction, in particular according to the references relating to protective groups cited above. The protective radical is more particularly the benzyloxycarbonyl radical. In this case, the hydrogenation reaction leads directly to the deprotection of the amine.

The quinolylpropylpiperidine derivative of general formula (VI) may be prepared by condensing a quinoline derivative of general formula (VII):

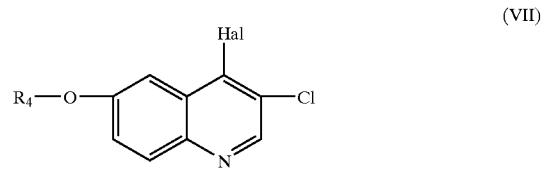

(VII)

in which $R_4$ is as defined above and Hal represents an iodine or bromine atom, with a piperidine derivative of general formula (VIII):

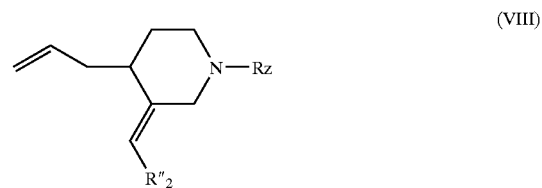

(VIII)

in which $R''_2$ is as defined above and $R_z$ represents an amino-protecting radical.

The reaction is carried out by the successive action of an organoborane (9-borabicyclo[3.3.1]nonane for example) in a solvent such as an ether (tetrahydrofuran, dioxane for example) at a temperature in the range of from about −20° C. to about 20° C., followed by a quinoline derivative of general formula (VII), by analogy with the methods described by Suzuki et al., Pure and Appl. Chem., 57, 1749 (1985) and removal of the amino-protecting radical $R_2$. The reaction is generally carried out in the presence of a palladium salt (palladiumdiphenylphosphinoferrocene chloride for example) and of a base such as potassium phosphate, at a temperature in the range of from about 20° C. and the reflux temperature of the solvent.

The removal of the radical $R_2$ is carried out according to the known methods mentioned above, mentioned in the examples or described by T. W. Greene and P. G. M. Wuts, Protective Groups in Organic Synthesis (2nd ed.), A. Wiley—Interscience Publication (1991), or by McOmie, Protective Groups in Organic Chemistry, Plenum Press (1973).

The piperidine derivative of general formula (VIII) may be prepared by the Wittig reaction, by condensing a phosphorus ylide with a piperidine derivative of general formula (IX):

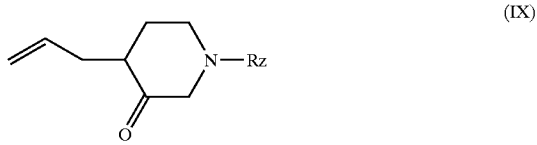

(IX)

in which Rz is as defined above.

The procedure is advantageously carried out using methyl (triphenylphosphoranylidene)acetate, in a solvent such as for example toluene, at a temperature in the range of from about 20° C. to about 110° C.

The 3-oxopiperidine derivative of general formula (IX) may be prepared according to or by analogy with the method described by Y. Takeuchi et al., Synthesis, 10, 1814 (1999).

The quinoline derivatives of general formula (VII) may be prepared according to the method described in patent application WO 200240474-A2.

The quinolylpropylpiperidine derivative of general formula (II), for which $R'_2$ is a protected carboxyl radical and $R'_{1a}$ and $R_{1b}$ are hydrogen atoms, may be prepared from the corresponding derivative for which $R'_2$ is protected carboxymethyl, by reducing this radical to a hydroxyethyl radical, converting to a p-toluenesulfonyloxyethyl derivative, and then converting this derivative to a vinyl derivative by an elimination reaction followed by the oxidation of the derivative obtained to a carboxyl derivative and the introduction of the protective group onto the carboxyl radical thus obtained.

The reduction of the protected acid to a hydroxyethyl radical is carried out according to the customary methods which do not adversely affect the rest of the molecule, in particular the procedure is carried out by the action of a hydride (lithium and aluminum hydride or diisobutylaluminum hydride for example) in a solvent such as an ether (tetrahydrofuran for example) at a temperature in the range of from about 20° C. to about 60° C.

The conversion of the hydroxyethyl derivative to a p-toluenesulfonyloxyethyl derivative is carried out in particular according to the method described by L. F. Fieser and M. Fieser, Reagents for Organic Synthesis, vol. 1, 1179 (1967), starting with p-toluenesulfonyl chloride in the presence of a base such as a tertiary amine (for example triethylamine) or an aromatic amine (for example pyridine), in a halogenated solvent (for example dichloromethane) or without solvent, at a temperature in the range of from about 0° C. to about 50° C.

The conversion of the p-toluenesulfonyloxy-ethyl derivative to a vinyl derivative is carried out by an elimination reaction, in particular according to the method described by A. Sharma et al., Org. Prep Proced. Int., 25(3), 330–333 (1993), in the presence of a base such as for example potassium t-butoxide in a solvent such as dimethylsulfoxide for example, at a temperature in the range of from about 20° C. to about 100° C.

The conversion of the vinyl derivative to a carboxyl derivative is carried out by the oxidation methods described in the literature, in particular using sodium metaperiodate in the presence of ruthenium trichloride hydrate, in a mixture of solvents such as for example the water/acetonitrile mixture, at a temperature in the range of from about 20° C. to about 60° C.

According to an alternative, the quinolylpropylpiperidine derivative of general formula (II), for which $R'_{1a}$ and $R_{1b}$ are hydrogen atoms may be prepared by condensing a quinoline derivative of general formula (VII) as defined above, with a piperidine derivative of general formula (X):

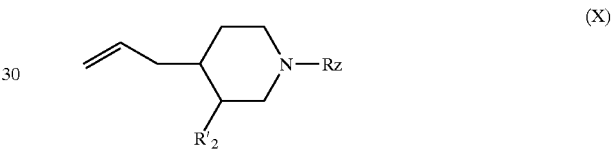

(X)

in which Rz and $R'_2$ are as defined above, to obtain a derivative of general formula (XI)

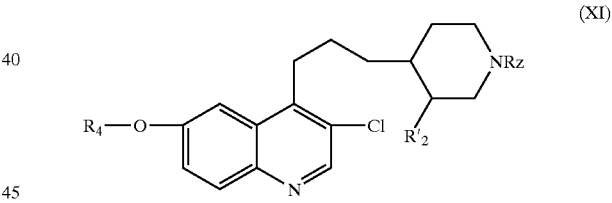

(XI)

and then removing the amino-protecting radical Rz.

The reaction is carried out under conditions similar to the conditions described for the reaction of the quinoline derivative of general formula (VII) and of the piperidine derivative of general formula (VIII).

The removal of the radical Rz is carried out according to the known methods mentioned above.

According to the invention, the derivatives corresponding to those of general formula (XI) above, in which $R'_2$ represents a protected carboxyl radical, can be converted to derivatives in which $R'_2$ represents a carboxymethyl radical, under conditions similar to those described above, that is to say by reduction of the protected carboxyl to hydroxymethyl and conversion thereof to carboxymethyl.

The piperidine derivative of general formula (X) may be prepared by radical deoxygenation, using tributyltin hydride in the presence of 2-2'-azobisisobutyronitrile (AIBN), of a compound of general formula (XII):

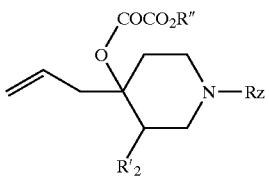

(XII)

in which R″ represents an alkyl radical, preferably methyl, and R′$_2$ and Rz are as defined above.

The radical deoxygenation reaction is carried out with tributyltin hydride in the presence of AIBN in an inert solvent, such as toluene or benzene, at a temperature in the range of from about 20° C. and the reflux temperature of the reaction medium, by analogy with the method described in J. Org. Chem., 1996, 61, 7189.

The piperidine derivative of general formula (XII) may be obtained by the action of an alkyl oxalyl halide, such as methyl oxalyl chloride, on a derivative of general formula (XIII):

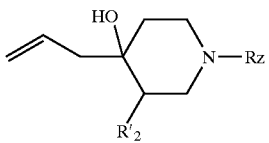

(XIII)

in which R′$_2$ and Rz are as defined above.

This reaction is carried out in the presence of a base such as 4-dimethylaminopyridine in an inert solvent such as acetonitrile or dichloromethane, at a temperature in the range of from about 0° C. to about 50° C., by analogy with the method described in J. Org. Chem., 1996, 61, 7189.

The piperidine derivative of general formula (XIII), in which R′$_2$ is a protected carboxyl radical and Rz is defined above, may be obtained by an allylation reaction of the ketoester of general formula (XIV)

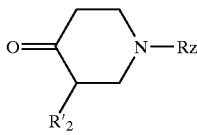

(XIV)

for which R′$_2$ and Rz are as defined above.

When R′$_2$ represents a protected carboxyl radical, this allylation reaction is carried out either using allyl bromide, zinc and ammonium chloride in an inert solvent such as tetrahydrofuran or dioxane, at a temperature in the range of from about 20° C. and the reflux temperature of the solvent, by analogy with the method described in J. Chem. Soc. Chem. Comm., 1994, 1217, or using allyl bromide in the presence of indium in a mixture of alcohol, such as methanol or ethanol, and water, at a temperature in the range of from about 20° C. to about 70° C., by analogy with the method described in Tetrahedron Letters, 1998, 54, 2347.

When R′$_2$ represents a protected carboxymethyl radical, the alkylation can be carried out by a reaction of the Grignard type, using a suitable organometallic reagent.

The compounds of general formula (XIV) are known or can be prepared by known methods, for example from alkyl 4-oxo-3-piperidinecarboxylate, preferably methyl 4-oxo-3-piperidinecaroxylate by using or adapting the method described in Tetrahedron Letters, 1991, 32, 3643, or from alkyl 4-oxo-3-piperidineacetate or 4-oxo-3-piperidineacetic acid, in which the nitrogen atom is protected. Such derivatives are described, for example, in Chem. Pharm. Bull (1983), 31 (11), 4135-8 or in Japanese application JP 54098771 or 56038147.

The various intermediates of quinolylpropylpiperidine type for which R$_4$ represents alkenyl-CH$_2$—, alkynyl-CH$_2$—, cycloalkyl or cycloalkyl-alkyl may be obtained by analogy with the preparation of the intermediates for which R$_4$ is alkyl, by the action of the corresponding halogenated derivative on the quinoline derivative hydroxylated at the 6-position.

It is understood that the derivatives of general formula (I), but also the intermediates of formulae (II), (III) and (IV) and also their preparation intermediates have a "cis/trans" isomerism at the level of the substituents at the 3- and 4-position of piperidine. The derivatives of the "trans" configuration may be obtained from the derivatives of the "cis" configuration according to or by analogy with the method described in International Application WO 99/37635, or from intermediates which exist in the form of mixtures, after separation according to known methods.

The quinolylpropylpiperidine derivatives of general formula (I) may be purified, where appropriate by physical methods such as crystallization or chromatography.

Moreover, it is also understood that, firstly, for the compounds of general formula (I) when R$_{1b}$ is a hydrogen atom and R$_{1a}$ is other than a hydrogen atom and, secondly, for the compounds of general formula (XII) and (XIII), enantiomeric and diastereoisomeric forms also exist, which forms, and also their mixtures, fall into the context of the present invention. The latter may be, where appropriate, separated in particular by chromatography on silica or by High-Performance Liquid Chromatography (HPLC). Likewise, the cis and trans derivatives may be separated by chromatography on silica or by High-Performance Liquid Chromatography (HPLC).

The quinolylpropylpiperidine derivatives of general formula (I) may be converted to addition salts with acids, by known methods. It is understood that these salts also fall within the scope of the present invention.

As examples of addition salts with pharmaceutically acceptable acids, there may be mentioned the salts formed with inorganic acids (hydrochlorides, hydrobromides, sulfates, nitrates, phosphates) or with organic acids (succinates, fumarates, tartarates, acetates, propionates, maleates, citrates, methanesulfonates, ethanesulfonates, phenylsulfonate, p-toluenesulfonates, isethionates, naphthylsulfonates or camphorsulfonates, or with substitution derivatives of these compounds).

Some of the quinolylpropylpiperidine derivatives of general formula (I) carrying a carboxyl radical may be converted to the form of metal salts or to addition salts with the nitrogen bases according to methods known per se. These salts also fall within the scope of the present invention. The salts may be obtained by the action of a metal (for example an alkali or alkaline-earth metal) base, of ammonia or of an amine, on a product according to the invention, in an appropriate solvent such as an alcohol, an ether or water, or by an exchange reaction with a salt of an organic acid. The salt formed precipitates after optional concentration of the solution, it is separated by filtration, decantation or freeze-drying. As examples of pharmaceutically acceptable salts, there may be mentioned the salts with alkali metals (sodium, potassium, lithium) or with alkaline-earth metals (magnesium, calcium), the ammonium salt, the salts of nitrogen bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine, dibenzylamine).

The quinolylpropylpiperidine derivatives according to the invention are particularly advantageous antibacterial agents.

In vitro, on gram-positive microbes, the quinolylpropylpiperidine derivatives according to the invention have proved active at concentrations of between 0.03 and 4 µg/ml on meticillin-resistant *Staphylococcus aureus* AS5155, also at concentrations of between 0.06 and 8 µg/ml on *Streptococcus pneumoniae* 6254-01 and at concentrations of between 0.06 and 64 µg/ml on *Enterococcus faecium* H983401, and on gram-negative microbes they have proved active at concentrations of between 0.12 and 32 µg/ml on *Moraxella catharrhalis* IPA152; in vivo, they have proved active on experimental infections of mice with *Straphylococcus aureus* IP8203 at doses of between 12 and 150 mg/kg by the subcutaneous route ($CD_{50}$) and for some of them at doses of between 26 and 150 mg/kg by the oral route.

Moreover, the products according to the invention are particularly advantageous because of their low toxicity. None of the products exhibited toxicity at the dose of 100 mg/kg by the subcutaneous route in mice.

These properties make said products, and also their salts of pharmaceutically acceptable acids and bases suitable for use as medicaments in the treatment of ailments with sensitive microorganisms caused by gram⊕ bacteria, and in particular in that of staphylococcic infections, such as staphylococcal septicemias, malignant staphylococcic infections of the face or skin, pyoderma, septic or suppurant wounds, anthrax, phlegmons, erysipelas, acute primary or post-influenza, staphylococcic infections, bronchopneumonias or pulmonary suppurations.

These products can also be used as medicaments in the treatment of colibacilloses and related infections, in infections with proteus, with klebsiella and with salmonella, and in other ailments caused by gram (-) bacteria.

The subject of the present invention is therefore also, as medicaments, and in particular medicaments intended for the treatment of bacterial infections in humans or animals, the compounds of formula (I) as defined above, and also their pharmaceutically acceptable salts, and in particular the preferred compounds mentioned above.

The present invention also relates to the pharmaceutical compositions containing at least one quinolylpropylpiperidine derivative according to the invention, where appropriate in the form of a salt, in the pure state, or in the form of a combination with one or more compatible and pharmaceutically acceptable diluents or adjuvants.

The compositions according to the invention can be used orally, parenterally, topically, rectally or as aerosols.

As solid compositions for oral administration, use may be made of tablets, pills, gelatin capsules, powders or granules. In these compositions, the active product according to the invention is mixed with one or more inert diluents or adjuvants, such as sucrose, lactose or starch. These compositions can comprise substances other than diluents, for example a lubricant such as magnesium stearate or a coating intended for a controlled release.

As liquid compositions for oral administration, use may be made of pharmaceutically acceptable solutions, suspensions, emulsions, syrups and elixirs containing inert diluents such as water or paraffin oil. These compositions can also comprise substances other than diluents, for example wetting, sweetening or flavoring products.

The compositions for parenteral administration can be sterile solutions or emulsions. As solid or vehicle, use may be made of water, propylene glycol, a polyethylene glycol, plant oils, in particular olive oil, and/or injectable organic esters, for example ethyl oleate. These compositions can also contain adjuvants, in particular wetting agents, isotonicity agents, emulsifiers, dispersing agents and stabilizers.

The sterilization can be carried out in several ways, for example using a bacteriological filter, by irradiation or by heating. They can also be prepared in the form of sterile solid compositions which can be dissolved at the time of use in sterile water or any other injectable sterile medium.

The compositions for topical administration can, for example, be creams, ointments, lotions or aerosols.

The compositions for rectal administration are suppositories or rectal capsules, which contain, besides the active principle, excipients such as cacao butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in serum or in any other pharmaceutically acceptable vehicle. For use in the form of dry aerosols intended to be directly inhaled, the active principle is finely divided up and combined with a water-soluble solid diluent or vehicle with a particle size of 30 to 80 µm, for example dextran, mannitol or lactose.

In human therapy, the novel quinolylpropylpiperidine derivatives according to the invention are particularly useful in the treatment of infections of bacterial origin. The doses depend on the desired effect and on the duration of treatment. The physician will determine the dosage which he or she considers to be the most suitable as a function of the treatment, as a function of age, of weight and of the degree of infection, and of the other factors specific to the individual to be treated. In general, the doses are between 750 mg and 3 g of active product taken in 2 or 3 doses per day orally, or between 400 mg and 1.2 g taken intravenously, for an adult.

The following example illustrates a composition according to the invention.

A liquid composition intended for parenteral use is prepared according to the usual technique, comprising:

| | |
|---|---|
| (3R, 4R)-4-[3-(S)-hydroxy-(3-chloro-6-methoxyquinolin-4-yl)propyl]-1-[2-(2,5-difluorophenylthio)ethyl]piperidine-3-carboxylic acid | 1 g |
| Glucose | qs 2.5% |
| Sodium hydroxide | qs pH = 4–4.5 |
| Water for inlectable preparation | qs 20 ml | qs = in sufficient quantities up to

Finally, a subject of the invention is, as novel industrial products, and in particular as intermediate products required for the preparation of the products of formula (I):

the products of formula (II) as defined above;
the products of formula (A)

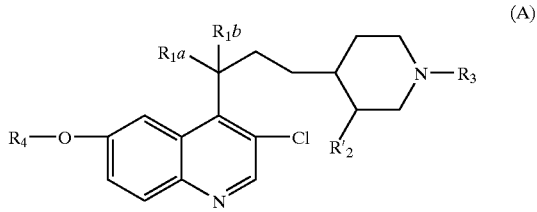

(A)

in which $R_{1a}$, $R_{1b}$, $R'_2$, $R_3$ and $R_4$ are as defined above, corresponding to the products of formula (III) or obtained intermediately at the end of the various treatments carried out on the products of formula (III);

the products of formula (IV) as defined above;
the products of formula (VI) as defined above;
the products of formula (XI) as defined above;
the products of formula (VIII), (IX), (X), (XII) and (XIII) as defined above.

Among the products according to the invention, those which are more particularly advantageous are the quinolyl-propylpiperidine derivatives mentioned hereinafter, and in particular those described in the examples, without limitation:

(3RS,4RS) or (3SR,4RS)-4-[3-(3-chloro-6-methoxyquinolin-4-yl)propyl]-1-(2-phenylthioethyl)piperidine-3-carboxylic acid (3RS,4RS) or (3SR,4RS)-4-[3-(3-chloro-6-methoxyquinolin-4-yl)propyl]-1-[2-(3-fluorophenylthio)ethyl]piperidine-3-carboxylic acid (3RS,4RS) or (3SR,4RS)-4-[3-(3-chloro-6-methoxyquinolin-4-yl)propyl]-1-[2-(2,5-difluorophenylthio)ethyl]piperidine-3-carboxylic acid (3RS,4RS) or (3SR,4RS)-4-[3-(3-chloro-6-methoxyquinolin-4-yl)propyl]-1-[2-(3,5-difluorophenylthio)ethyl]piperidine-3-carboxylic acid (3RS,4RS) or (3SR,4RS)-4-[3-(3-chloro-6-methoxyquinolin-4-yl)propyl]-1-[2-(2,3,5-trifluorophenylthio)ethyl]piperidine-3-carboxylic acid (3RS,4RS) or (3SR,4RS)-4-[3-(3-chloro-6-methoxyquinolin-4-yl)propyl]-1-[2-(n-propylthio)ethyl]piperidine-3-carboxylic acid (3RS,4RS) or (3SR,4RS)-4-[3-(3-chloro-6-methoxyquinolin-4-yl)propyl]-1-[2-(n-butylthio)ethyl]piperidine-3-carboxylic acid (3RS,4RS) or (3SR,4RS)-4-[3-(3-chloro-6-methoxyquinolin-4-yl)propyl]-1-[2-(cyclopropylthio)ethyl]piperidine-3-carboxylic acid (3RS,4RS) or (3SR,4RS)-4-[3-(3-chloro-6-methoxyquinolin-4-yl)propyl]-1-[2-(cyclobutylthio)ethyl]piperidine-3-carboxylic acid (3RS,4RS) or (3SR,4RS)-4-[3-(3-chloro-6-methoxyquinolin-4-yl)propyl]-1-[2-(cyclopentylthio)ethyl]piperidine-3-carboxylic acid (3RS,4RS) or (3SR,4RS)-4-[3-(3-chloro-6-methoxyquinolin-4-yl)propyl]-1-[2-(cyclohexylthio)ethyl]piperidine-3-carboxylic acid (3RS,4RS) or (3SR,4RS)-4-[3-(3-chloro-6-methoxyquinolin-4-yl)propyl]-1-[2-(thien-2-yl)thioethyl]piperidine-3-carboxylic acid (3RS,4RS) or (3SR,4RS)-4-[3-(3-chloro-6-methoxyquinolin-4-yl)propyl]-1-[2-(5-fluorothien-2-yl)thioethyl]piperidine-3-carboxylic acid (3RS,4RS) or (3SR,4RS)-4-[3-(3-chloro-6-methoxyquinolin-4-yl)propyl]-1-[2-(4-fluorothien-2-yl)thioethyl]piperidine-3-carboxylic acid (3RS,4RS) or (3SR,4RS)-4-[3-(3-chloro-6-methoxyquinolin-4-yl)propyl]-1-[2-(3-fluorothien-2-yl)thioethyl]piperidine-3-carboxylic acid (3RS,4RS) or (3SR,4RS)-4-[3-(3-chloro-6-methoxyquinolin-4-yl)propyl]-1-[2-(thien-3-yl)thioethyl]piperidine-3-carboxylic acid (3RS,4RS) or (3SR,4RS)-4-[3-(3-chloro-6-methoxyquinolin-4-yl)propyl]-1-[2-(1,3-thiazol-2-yl)thioethyl]piperidine-3-carboxylic acid (3RS,4RS) or (3SR,4RS)-4-[3-(3-chloro-6-methoxyquinolin-4-yl)propyl]-1-[2-(pyridine-2-yl)thioethyl]piperidine-3-carboxylic acid (3RS,4RS) or (3SR,4RS)-4-[3-(3-chloro-6-methoxyquinolin-4-yl)propyl]-1-[2-(4-fluoropyridin-2-yl)thioethyl]piperidine-3-carboxylic acid (3RS,4RS) or (3SR,4RS)-4-[3-(3-chloro-6-methoxyquinolin-4-yl)propyl]-1-[2-(3-fluoropyridin-2-yl)thioethyl]piperidine-3-carboxylic acid (3RS,4RS) or (3SR,4RS)-4-[3-(3-chloro-6-methoxyquinolin-4-yl)propyl]-1-[3-(3-fluorophenyl)prop-2-ynyl]piperidine-3-carboxylic acid (3RS,4RS) or (3SR,4RS)-4-[3-(3-chloro-6-methoxyquinolin-4-yl)propyl]-1-[3-(2,5-difluorophenyl)prop-2-ynyl]piperidine-3-carboxylic acid (3RS,4RS) or (3SR,4RS)-4-[3-(3-chloro-6-methoxyquinolin-4-yl)propyl]-1-[3-(3,5-difluorophenyl)prop-2-ynylpiperidine-3-carboxylic acid (3RS,4RS) or (3SR,4RS)-4-[3-(3-chloro-6-methoxyquinolin-4-yl)propyl]-1-[3-(2,3,5-trifluorophenyl)prop-2-ynyl]piperidine-3-carboxylic acid (3RS,4RS) or (3SR,4RS)-4-[3-(3-chloro-6-methoxyquinolin-4-yl)propyl]-1-[3-(thien-2-yl)prop-2-ynyl]piperidine-3-carboxylic acid (3RS,4RS) or (3SR,4RS)-4-[3-(3-chloro-6-methoxyquinolin-4-yl)propyl]-1-[3-(5-fluorothien-2-yl)prop-2-ynyl]piperidine-3-carboxylic acid (3RS,4RS) or (3SR,4RS)-4-[3-(3-chloro-6-methoxyquinolin-4-yl)propyl]-1-[3-(4-fluorothien-2-yl)prop-2-ynyl]piperidine-3-carboxylic acid (3RS,4RS) or (3SR,4RS)-4-[3-(3-chloro-6-methoxyquinolin-4-yl)propyl]-1-[3-(3-fluorothien-2-yl)prop-2-ynyl]piperidine-3-carboxylic acid (3RS,4RS) or (3SR,4RS)-4-[3-(3-chloro-6-methoxyquinolin-4-yl)propyl]-1-[3-(thien-3-yl)prop-2-ynyl]piperidine-3-carboxylic acid (3RS,4RS) or (3SR,4RS)-4-[3-(R,S)-hydroxy-3-(3-chloro-6-methoxyquinolin-4-yl)proyl]-1-(2-phenylthioethyl)piperidine-3-carboxylic acid (3RS,4RS) or (3SR,4RS)-4-[3-(R,S)-hydroxy-3-(3-chloro-6-methoxyquinolin-4-yl)proyl]-1-[2-(3-fluorophenylthio)ethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(2,5-difluorophenylthio)ethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(3,5-difluorophenylthio)ethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(2,3,5-trifluorophenylthio)ethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(n-propylthio)ethyl]piperidine-3-carboxylic acid (3RS,4RS) or (3SR,4RS)-4-[3-(R,S)-hydroxy-3-(3-chloro-6-methoxyquinolin-4-yl)proyl]-1-[2-(n-butylthio)ethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(cyclopropylthio)ethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(cyclobutylthio)ethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(cyclopentylthio)ethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(cyclohexylthio)ethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(thien-2-yl)-thioethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(5-fluorothien-2-yl)thioethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(4-fluorothien-2-yl)thioethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(3-fluorothien-2-yl)thioethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(thien-3-yl)thioethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(1,3-thiazol-2-yl)thioethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(pyridin-2-yl)thioethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(4-fluoropyridin-2-yl)thioethyl]piperidine-3-carboxylic acid (3RS,4RS) or (3SR,4RS)-4-[3-(R,S)-hydroxy-3-(3-chloro-6-methoxyquinolin-4-yl)propyl]-1-[2-(3-fluoropyridin-2-yl)thioethyl]piperidine-3-carboxylic acid (3RS,4RS) or (3SR,4RS)-4-[3-(R,S)-hydroxy-3-(3-chloro-6-methoxyquinolin-4-yl)propyl]-1-[3-(3-fluorophenyl)prop-2-ynyl]piperidine-3-carboxylic acid (3RS,4RS) or (3SR,4RS)-4-[3-(R,S)-hydroxy-3-(3-chloro-6-methoxyquinolin-4-yl)propyl]-1-[3-(2,5-difluorophenyl)prop-2-ynyl]piperidine-3-carboxylic acid (3RS,4RS) or (3SR,4RS)-4-[3-(R,S)-hydroxy-3-(3-chloro-6-methoxyquinolin-4-yl)propyl]-1-[3-(3,5-difluorophenyl)prop-2-ynyl]piperidine-3-carboxylic acid (3RS,4RS) or (3SR,4RS)-4-[3-(R,S)-hydroxy-3-(3-chloro-6-methoxyquinolin-4-yl)propyl]-1-[3-(2,3,5-trifluorophenyl)prop-2-ynyl]piperidine-3-carboxylic acid (3RS,4RS) or (3SR,4RS)-4-[3-(R,S)-hydroxy-3-(3-chloro-6-methoxyquinolin-4-yl)propyl]-1-[3-(thien-2-yl)prop-2-ynyl]piperidine-3-carboxylic acid (3RS,4RS) or (3SR,4RS)-4-[3-(R,S)-hydroxy-3-(3-chloro-6-methoxyquinolin-4-yl)propyl]-1-[3-(5-fluorothien-2-yl)prop-2-ynyl]piperidine-3-carboxylic acid (3RS,4RS) or (3SR,4RS)-4-[3-(R,S)-hydroxy-3-(3-chloro-6-methoxyquinolin-4-yl)propyl]-1-[3-(4-fluorothien-2-yl)prop-2-ynyl]piperidine-3-carboxylic acid (3RS,4RS) or (3SR,4RS)-4-[3-(R,S)-hydroxy-3-(3-chloro-6-methoxyquinolin-4-yl)propyl]-1-[3-(3-fluorothien-2-yl)prop-2-ynyl]piperidine-3-carboxylic acid (3RS,4RS) or (3SR,4RS)-4-[3-(R,S)-hydroxy-3-(3-chloro-6-methoxyquinolin-4-yl)propyl]-1-[3-(thien-3-yl)prop-2-ynyl]piperidine-3-carboxylic acid (3RS,4RS) or (3SR,4RS)-4-[3-(R,S)-fluoro-3-(3-chloro-6-methoxyquinolin-4-yl)propyl]-1-(2-phenylthioethyl)piperidine-3-carboxylic acid (3RS,4RS) or (3SR,4RS)-4-[3-(R,S)-fluoro-3-(3-chloro-6-methoxyquinolin-4-yl)propyl]-1-[2-(3-fluorophenylthio)-ethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(2,5-difluorophenylthio)-ethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(3,5-difluorophenylthio)-ethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(2,3,5-trifluorophenylthio)-ethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(n-propylthio)ethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(n-butylthio)ethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(cyclopropylthio)ethyl]iperidine-3-carboxylic acid (3RS,4RS) or (3SR,4RS)-4-[3-(R,S)-fluoro-3-(3-chloro-6-methoxyquinolin-4-yl)propyl]-1-[2-(cyclobutylthio)ethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(cyclopentylthio)ethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(cyclohexylthio)ethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(thien-2-yl)thioethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(5-fluorothien-2-yl)thioethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(4-fluorothien-2-yl)thioethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(3-fluorothien-2-yl)thioethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(thien-3-yl)thioethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(1,3-thiazol-2-yl)thioethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(pyridin-2-yl)thioethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(4-fluoropyridin-2-yl)thioethyl]piperidine-3-carboxylic acid (3RS,4RS) or (3SR,4RS)-4-[3-(R,S)-fluoro-3-(3-chloro-6-methoxyquinolin-4-yl)propyl]-1-[2-(3-fluoropyridin-2-yl)thioethyl]piperidine-3-carboxylic acid (3RS,4RS) or (3SR,4RS)-4-[3-(R,S)-fluoro-3-(3-chloro-6-methoxyquinolin-4-yl)propyl]-1-[3-(3-fluorophenyl)-prop-2-ynyl]piperidine-3-carboxylic acid (3RS,4RS) or (3SR,4RS)-4-[3-(R,S)-fluoro-3-(3-chloro-6-methoxyquinolin-4-yl)propyl]-1-[3-(2,5-difluorophenyl)-prop-2-ynyl]piperidine-3-carboxylic acid (3RS,4RS) or (3SR,4RS)-4-[3-(R,S)-fluoro-3-(3-chloro-6-methoxyquinolin-4-yl)propyl]-1-[3-(3,5-difluorophenyl)-prop-2-ynyl]piperidine-3-carboxylic acid (3RS,4RS) or (3SR,4RS)-4-[3-(R,S)-fluoro-3-(3-chloro-6-methoxyquinolin-4-yl)propyl]-1-[3-(2,3,5-trifluorophenyl)prop-2-ynyl]piperidine-3-carboxylic acid (3RS,4RS) or (3SR,4RS)-4-[3-(R,S)-fluoro-3-(3-chloro-6-methoxyquinolin-4-yl)propyl]-1-[3-(thien-2-yl)prop-2-ynyl]piperidine-3-carboxylic acid (3RS,4RS) or (3SR,4RS)-4-[3-(R,S)-fluoro-3-(3-chloro-6-methoxyquinolin-4-yl)propyl]-1-[3-(5-fluorothien-2-yl)-prop-2-ynyl]piperidine-3-carboxylic acid (3RS,4RS) or (3SR,4RS)-4-[3-(R,S)-fluoro-3-(3-chloro-6-methoxyquinolin-4-yl)propyl]-1-[3-(4-fluorothien-2-yl)-prop-2-ynyl]piperidine-3-carboxylic acid (3RS,4RS) or (3SR,4RS)-4-[3-(R,S)-fluoro-3-(3-chloro-6-methoxyquinolin-4-yl)propyl]-1-[3-(3-fluorothien-2-yl)-prop-2-ynyl]piperidine-3-carboxylic acid (3RS,4RS) or (3SR,4RS)-4-[3-(R,S)-fluoro-3-(3-chloro-6-methoxyquinolin-4-yl)propyl]-1-[3-(thien-3-yl)prop-2-ynyl]piperidine-3-carboxylic acid (3RS,4RS) or (3SR,4RS)-4-[3-(R,S)-amino-3-(3-chloro-6-methoxyquinolin-4-yl)propyl]-1-(2-phenylthioethyl)piperidine-3-carboxylic acid (3RS,4RS) or (3SR,4RS)-4-[3-(R,S)-amino-3-(3-chloro-6-methoxyquinolin-4-yl)propyl]-1-[2-(3-fluorophenylthio)ethyl]piperidine-3-carboxylic acid (3RS,4RS) or (3SR,4RS)-4-[3-(R,S)-amino-3-(3-chloro-6-methoxyquinolin-4-yl)propyl]-1-[2-(2,5-difluorophenylthio)-ethyl]piperidine-3-carboxylic acid (3RS,4RS) or (3SR,4RS)-4-[3-(R,S)-amino-3-(3-chloro-6-methoxyquinolin-4-yl)propyl]-1-[2-(3,5-difluorophenylthio)ethyl]piperidine-3-carboxylic acid (3RS,4RS) or (3SR,4RS)-4-[3-(R,S)-amino-3-(3-chloro-6-methoxyquinolin-4-yl)propyl]-1-[2-(2,3,5-trifluorophenylthio)-ethyl]piperidine-3-carboxylic acid (3RS,4RS) or (3SR,4RS)-4-[3-(R,S)-amino-3-(3-chloro-6-methoxyquinolin-4-yl)propyl]-1-[2-(n-propylthio)ethyl]piperidine-3-carboxylic acid (3RS,4RS) or (3SR,4RS)-4-[3-(R,S)-amino-3-(3-chloro-6-methoxyquinolin-4-yl)propyl]-1-[2-(n-butylthio)ethyl]piperidine-3-carboxylic acid (3RS,4RS) or (3SR,4RS)-4-[3-(R,S)-amino-3-(3-chloro-6-methoxyquinolin-4-yl)propyl]-1-[2-(cyclopropylthio)ethyl]piperidine-3-carboxylic acid (3RS,4RS) or (3SR,4RS)-4-[3-(R,S)-amino-3-(3-chloro-6-methoxyquinolin-4-yl)propyl]-1-[2-(cyclobutylthio)ethyl]piperidine-3-carboxylic acid (3RS,4RS) or (3SR,4RS)-4-[3-(R,S)-amino-3-(3-chloro-6-methoxyquinolin-4-yl)propyl]-1-[2-(cyclopentylthio)ethyl]piperidine-3-carboxylic acid (3RS,4RS) or (3SR,4RS)-4-[3-(R,S)-amino-3-(3-chloro-6-methoxyquinolin-4-yl)propyl]-1-[2-(cyclohexylthio)ethyl]piperidine-3-carboxylic acid (3RS,4RS) or (3SR,4RS)-4-[3-(R,S)-amino-3-(3-chloro-6-methoxyquinolin-4-yl)propyl]-1-[2-(thien-2-yl)thioethyl]piperidine-3-carboxylic acid (3RS,4RS) or (3SR,4RS)-4-[3-(R,S)-amino-3-(3-chloro-6-methoxyquinolin-4-yl)propyl]-1-[2-(5-fluorothien-2-yl)thioethyl]piperidine-3-carboxylic acid (3RS,4RS) or (3SR,4RS)-4-[3-(R,S)-amino-3-(3-chloro-6-methoxyquinolin-4-yl)propyl]-1-[2-(4-fluorothien-2-yl)thioethyl]piperidine-3-carboxylic acid (3RS,4RS) or (3SR,4RS)-4-[3-(R,S)-amino-3-(3-chloro-6-methoxyquinolin-4-yl)propyl]-1-[2-(3-fluorothien-2-yl)thioethyl]piperidine-3-carboxylic acid (3RS,4RS) or (3SR,4RS)-4-[3-(R,S)-amino-3-(3-chloro-6-methoxyquinolin-4-yl)propyl]-1-[2-(thien-3-yl)thioethyl]piperidine-3-carboxylic acid (3RS,4RS) or (3SR,4RS)-4-[3-(R,S)-amino-3-(3-chloro-6-methoxyquinolin-4-yl)propyl]-1-[2-(1,3-thiazol-2-yl)thioethyl]piperidine-3-carboxylic acid (3RS,4RS) or (3SR,4RS)-4-[3-(R,S)-amino-3-(3-chloro-6-methoxyquinolin-4-yl)propyl]-1-[2-(pyridin-2-yl)thioethyl]piperidine-3-carboxylic acid (3RS,4RS) or (3SR,4RS)-4-[3-(R,S)-amino-3-(3-chloro-6-methoxyquinolin-4-yl)propyl]-1-[2-(4-fluoropyridin-2-yl)thioethyl]piperidine-3-carboxylic acid (3RS,4RS) or (3SR,4RS)-4-[3-(R,S)-amino-3-(3-chloro-6-methoxyquinolin-4-yl)propyl]-1-[2-(3-fluoropyridin-2-yl)thioethyl]piperidine-3-carboxylic acid (3RS,4RS) or (3SR,4RS)-4-[3-(R,S)-amino-3-(3-chloro-6-methoxyquinolin-4-yl)propyl]-1-[3-(3-fluorophenyl)prop-2-ynyl]piperidine-3-carboxylic acid (3RS,4RS) or (3SR,4RS)-4-[3-(R,S)-amino-3-(3-chloro-6-methoxyquinolin-4-yl)propyl]-1-[3-(2,5-difluorophenyl)-prop-2-ynyl]piperidine-3-carboxylic acid (3RS,4RS) or (3SR,4RS)-4-[3-(R,S)-amino-3-(3-chloro-6-methoxyquinolin-4-yl)propyl]-1-[3-(3,5-difluorophenyl)-prop-2-ynyl]piperidine-3-carboxylic acid (3RS,4RS) or (3SR,4RS)-4-[3-(R,S)-amino-3-(3-chloro-6-methoxyquinolin-4-yl)propyl]-1-[3-(2,3,5-trifluorophenyl)prop-2-ynyl]piperidine-3-carboxylic acid (3RS,4RS) or (3SR,4RS)-4-[3-(R,S)-amino-3-(3-chloro-6-methoxyquinolin-4-yl)propyl]-1-[3-(thien-2-yl)prop-2-ynyl]piperidine-3-carboxylic acid (3RS,4RS) or (3SR,4RS)-4-[3-(R,S)-amino-3-(3-chloro-6-methoxyquinolin-4-yl)propyl]-1-[3-(5-fluorothien-2-yl)prop-2-ynyl]piperidine-3-carboxylic acid (3RS,4RS) or (3SR,4RS)-4-[3-(R,S)-amino-3-(3-chloro-6-methoxyquinolin-4-yl)propyl]-1-[3-(4-fluorothien-2-yl)prop-2-ynyl]piperidine-3-carboxylic acid (3RS,4RS) or (3SR,4RS)-4-[3-(R,S)-amino-3-(3-chloro-6-methoxyquinolin-4-yl)propyl]-1-[3-(3-fluorothien-2-yl)prop-2-ynyl]piperidine-3-carboxylic acid (3RS,4RS) or (3SR,4RS)-4-[3-(R,S)-amino-3-(3-chloro-6-methoxyquinolin-4-yl)propyl]-1-[3-(thien-3-yl)prop-2-ynyl]piperidine-3-carboxylic acid (3RS,4RS) or (3SR,4RS)-4-[3-oxo-3-(3-chloro-6-methoxyquinolin-4-yl)propyl]-1-(2-phenylthioethyl)piperidine-3-carboxylic acid (3RS,4RS) or (3SR,4RS)-4-[3-oxo-3-(3-chloro-6-methoxyquinolin-4-yl)propyl]-1-[2-(3-fluorophenylthio)-ethyl]piperidine-3-carboxylic acid (3RS,4RS) or (3SR,4RS)-4-[3-oxo-3-(3-chloro-6-methoxyquinolin-4-yl)propyl]-1-[2-(2,5-difluorophenylthio)ethyl]piperidine-3-carboxylic acid (3RS,4RS) or (3SR,4RS)-4-[3-oxo-3-(3-chloro-6-methoxyquinolin-4-yl)propyl]-1-[2-(3,5-difluorophenylthio)ethyl]piperidine-3-carboxylic acid (3RS,4RS) or (3SR,4RS)-4-[3-oxo-3-(3-chloro-6-methoxyquinolin-4-yl)propyl]-1-[2-(2,3,5-trifluorophenylthio)ethyl]piperidine-3-carboxylic acid (3RS,4RS) or (3SR,4RS)-4-[3-oxo-3-(3-chloro-6-methoxyquinolin-4-yl)propyl]-1-[2-(n-propylthio)ethyl]piperidine-3-carboxylic acid (3RS,4RS) or (3SR,4RS)-4-[3-oxo-3-(3-chloro-6-methoxyquinolin-4-yl)propyl]-1-[2-(n-butylthio)ethyl]piperidine-3-carboxylic acid (3RS,4RS) or (3SR,4RS)-4-[3-oxo-3-(3-chloro-6-methoxyquinolin-4-yl)propyl]-1-[2-(cyclopropylthio)ethyl]piperidine-3-carboxylic acid (3RS,4RS) or (3SR,4RS)-4-[3-oxo-3-(3-chloro-6-methoxyquinolin-4-yl)propyl]-1-[2-(cyclobutylthio)ethyl]piperidine-3-carboxylic acid (3RS,4RS) or (3SR,4RS)-4-[3-oxo-3-(3-chloro-6-methoxyquinolin-4-yl)propyl]-1-[2-(cyclopentylthio)ethyl]piperidine-3-carboxylic acid (3RS,4RS) or (3SR,4RS)-4-[3-oxo-3-(3-chloro-6-methoxyquinolin-4-yl)propyl]-1-[2-(cyclohexylthio)ethyl]piperidine-3-carboxylic acid (3RS,4RS) or (3SR,4RS)-4-[3-oxo-3-(3-chloro-6-methoxyquinolin-4-yl)propyl]-1-[2-(thien-2-yl)thioethyl]piperidine-3-carboxylic acid (3RS,4RS) or (3SR,4RS)-4-[3-oxo-3-(3-chloro-6-methoxyquinolin-4-yl)propyl]-1-[2-(5-fluorothien-2-yl)thioethyl]piperidine-3-carboxylic acid
(3RS,4RS) or (3SR,4RS)-4-[3-oxo-3-(3-chloro-6-methoxyquinolin-4-yl)propyl]-1-[2-(4-fluorothien-2-yl)thioethyl]piperidine-3-carboxylic acid
(3RS,4RS) or (3SR,4RS)-4-[3-oxo-3-(3-chloro-6-methoxyquinolin-4-yl)propyl]-1-[2-(3-fluorothien-2-yl)thioethyl]piperidine-3-carboxylic acid
(3RS,4RS) or (3SR,4RS)-4-[3-oxo-3-(3-chloro-6-methoxyquinolin-4-yl)propyl]-1-[2-(thien-3-yl)thioethyl]piperidine-3-carboxylic acid
(3RS,4RS) or (3SR,4RS)-4-[3-oxo-3-(3-chloro-6-methoxyquinolin-4-yl)propyl]-1-[2-(1,3-thiazol-2-yl)thioethyl]piperidine-3-carboxylic acid
(3RS,4RS) or (3SR,4RS)-4-[3-oxo-3-(3-chloro-6-methoxyquinolin-4-yl)propyl]-1-[2-(pyridin-2-yl)thioethyl]piperidine-3-carboxylic acid
(3RS,4RS) or (3SR,4RS)-4-[3-oxo-3-(3-chloro-6-methoxyquinolin-4-yl)propyl]-1-[2-(4-fluoropyridin-2-yl)thioethyl]piperidine-3-carboxylic acid
(3RS,4RS) or (3SR,4RS)-4-[3-oxo-3-(3-chloro-6-methoxyquinolin-4-yl)propyl]-1-[2-(3-fluoropyridin-2-yl)thioethyl]piperidine-3-carboxylic acid
(3RS,4RS) or (3SR,4RS)-4-[3-oxo-3-(3-chloro-6-methoxyquinolin-4-yl)propyl]-1-[3-(3-fluorophenyl)-prop-2-ynyl]piperidine-3-carboxylic acid
(3RS,4RS) or (3SR,4RS)-4-[3-oxo-3-(3-chloro-6-methoxyquinolin-4-yl)propyl]-1-[3-(3-fluorophenyl)-prop-2-ynyl]piperidine-3-carboxylic acid
(3RS,4RS) or (3SR,4RS)-4-[3-oxo-3-(3-chloro-6-methoxyquinolin-4-yl)propyl]-1-[3-(3,5-difluorophenyl)-prop-2-ynyl]piperidine-3-carboxylic acid
(3RS,4RS) or (3SR,4RS)-4-[3-oxo-3-(3-chloro-6-methoxyquinolin-4-yl)propyl]-1-[3-(2,3,5-trifluorophenyl)prop-2-ynyl]piperidine-3-carboxylic acid
(3RS,4RS) or (3SR,4RS)-4-[3-oxo-3-(3-chloro-6-methoxyquinolin-4-yl)propyl]-1-[3-(thien-2-yl)prop-2-ynyl]piperidine-3-carboxylic acid
(3RS,4RS) or (3SR,4RS)-4-[3-oxo-3-(3-chloro-6-methoxyquinolin-4-yl)propyl]-1-[3-(5-fluorothien-2-yl)prop-2-ynyl]piperidine-3-carboxylic acid
(3RS,4RS) or (3SR,4RS)-4-[3-oxo-3-(3-chloro-6-methoxyquinolin-4-yl)propyl]-1-[3-(4-fluorothien-2-yl)prop-2-ynyl]piperidine-3-carboxylic acid
(3RS,4RS) or (3SR,4RS)-4-[3-oxo-3-(3-chloro-6-methoxyquinolin-4-yl)propyl]-1-[3-(3-fluorothien-2-yl)prop-2-ynyl]piperidine-3-carboxylic acid
(3RS,4RS) or (3SR,4RS)-4-[3-oxo-3-(3-chloro-6-methoxyquinolin-4-yl)propyl]-1-[3-(thien-3-yl)prop-2-ynyl]piperidine-3-carboxylic acid
(3RS,4RS) or (3SR,4RS)-4-[3-(3-chloro-6-methoxyquinolin-4-yl)propyl]-1-(2-phenylthioethyl)piperidine-3-acetic acid
(3RS,4RS) or (3SR,4RS)-4-[3-(3-chloro-6-methoxyquinolin-4-yl)propyl]-1-[2-(3-fluorophenylthio)ethyl]piperidine-3-acetic acid
(3RS,4RS) or (3SR,4RS)-4-[3-(3-chloro-6-methoxyquinolin-4-yl)propyl]-1-[2-(2,5-difluorophenylthio)ethyl]piperidine-3-acetic acid
(3RS,4RS) or (3SR,4RS)-4-[3-(3-chloro-6-methoxyquinolin-4-yl)propyl]-1-[2-(3,5-difluorophenylthio)ethyl]piperidine-3-acetic acid
(3RS,4RS) or (3SR,4RS)-4-[3-(3-chloro-6-methoxyquinolin-4-yl)propyl]-1-[2-(2,3,5-trifluorophenylthio)ethyl]piperidine-3-acetic acid
(3RS,4RS) or (3SR,4RS)-4-[3-(3-chloro-6-methoxyquinolin-4-yl)propyl]-1-[2-(n-propylthio)ethyl]piperidine-3-acetic acid
(3RS,4RS) or (3SR,4RS)-4-[3-(3-chloro-6-methoxyquinolin-4-yl)propyl]-1-[2-(n-butylthio)ethyl]piperidine-3-acetic acid
(3RS,4RS) or (3SR,4RS)-4-[3-(3-chloro-6-methoxyquinolin-4-yl)propyl]-1-[2-(cyclopropylthio)ethyl]piperidine-3-acetic acid
(3RS,4RS) or (3SR,4RS)-4-[3-(3-chloro-6-methoxyquinolin-4-yl)propyl]-1-[2-(cyclobutylthio)ethyl]piperidine-3-acetic acid
(3RS,4RS) or (3SR,4RS)-4-[3-(3-chloro-6-methoxyquinolin-4-yl)propyl]-1-[2-(cyclopentylthio)ethyl]piperidine-3-acetic acid
(3RS,4RS) or (3SR,4RS)-4-[3-(3-chloro-6-methoxyquinolin-4-yl)propyl]-1-[2-(cyclohexylthio)ethyl]piperidine-3-acetic acid
(3RS,4RS) or (3SR,4RS)-4-[3-(3-chloro-6-methoxyquinolin-4-yl)propyl]-1-[2-(thien-2-yl)thioethyl]piperidine-3-acetic acid
(3RS,4RS) or (3SR,4RS)-4-[3-(3-chloro-6-methoxyquinolin-4-yl)propyl]-1-[2-(5-fluorothien-2-yl)thioethyl]piperidine-3-acetic acid
(3RS,4RS) or (3SR,4RS)-4-[3-(3-chloro-6-methoxyquinolin-4-yl)propyl]-1-[2-(4-fluorothien-2-yl)thioethyl]piperidine-3-acetic acid
(3RS,4RS) or (3SR,4RS)-4-[3-(3-chloro-6-methoxyquinolin-4-yl)propyl]-1-[2-(3-fluorothien-2-yl)thioethyl]piperidine-3-acetic acid
(3RS,4RS) or (3SR,4RS)-4-[3-(3-chloro-6-methoxyquinolin-4-yl)propyl]-1-[2-(thien-3-yl)thioethyl]piperidine-3-acetic acid
(3RS,4RS) or (3SR,4RS)-4-[3-(3-chloro-6-methoxyquinolin-4-yl)propyl]-1-[2-(1,3-thiazol-2-yl)thioethyl]piperidine-3-acetic acid
(3RS,4RS) or (3SR,4RS)-4-[3-(3-chloro-6-methoxyquinolin-4-yl)propyl]-1-[2-(pyridin-2-yl)thioethyl]piperidine-3-acetic acid
(3RS,4RS) or (3SR,4RS)-4-[3-(3-chloro-6-methoxyquinolin-4-yl)propyl]-1-[2-(4-fluoropyridin-2-yl)thioethyl]piperidine-3-acetic acid
(3RS,4RS) or (3SR,4RS)-4-[3-(3-chloro-6-methoxyquinolin-4-yl)propyl]-1-[2-(3-fluoropyridin-2-yl)thioethyl]piperidine-3-acetic acid
(3RS,4RS) or (3SR,4RS)-4-[3-(3-chloro-6-methoxyquinolin-4-yl)propyl]-1-[3-(3-fluorophenyl)prop-2-ynyl]piperidine-3-acetic acid
(3RS,4RS) or (3SR,4RS)-4-[3-(3-chloro-6-methoxyquinolin-4-yl)propyl]-1-[3-(2,5-difluorophenyl)prop-2-ynyl]piperidine-3-acetic acid
(3RS,4RS) or (3SR,4RS)-4-[3-(3-chloro-6-methoxyquinolin-4-yl)propyl]-1-[3-(3,5-difluorophenyl)prop-2-ynyl]piperidine-3-acetic acid
(3RS,4RS) or (3SR,4RS)-4-[3-(3-chloro-6-methoxyquinolin-4-yl)propyl]-1-[3-(2,3,5-trifluorophenyl)prop-2-ynyl]piperidine-3-acetic acid
(3RS,4RS) or (3SR,4RS)-4-[3-(3-chloro-6-methoxyquinolin-4-yl)propyl]-1-[3-(thien-2-yl)prop-2-ynyl]piperidine-3-acetic acid
(3RS,4RS) or (3SR,4RS)-4-[3-(3-chloro-6-methoxyquinolin-4-yl)propyl]-1-[3-(5-fluorothien-2-yl)prop-2-ynyl]piperidine-3-acetic acid
(3RS,4RS) or (3SR,4RS)-4-[3-(3-chloro-6-methoxyquinolin-4-yl)propyl]-1-[3-(4-fluorothien-2-yl)prop-2-ynyl]piperidine-3-acetic acid
(3RS,4RS) or (3SR,4RS)-4-[3-(3-chloro-6-methoxyquinolin-4-yl)propyl]-1-[3-(3-fluorothien-2-yl)prop-2-ynyl]piperidine-3-acetic acid
(3RS,4RS) or (3SR,4RS)-4-[3-(3-chloro-6-methoxyquinolin-4-yl)propyl]-1-[3-(thien-3-yl)prop-2-ynyl]piperidine-3-acetic acid (3RS,4RS) or (3SR,4RS)-4-[3-(R,S)-hydroxy-3-(3-chloro-6-methoxyquinolin-4-yl)propyl]-1-(2-phenylthioethyl)piperidine-3-acetic acid (3RS,4RS) or (3SR,4RS)-4-[3-(R,S)-hydroxy-3-(3-chloro-6-methoxyquinolin-4-yl)propyl]-1-[2-(3-fluorophenylthio)ethyl]piperidine-3-acetic acid (3RS,4RS) or (3SR,4RS)-4-[3-(R,S)-hydroxy-3-(3-chloro-6-methoxyquinolin-4-yl)propyl]-1-[2-(2,5-difluorophenylthio)ethyl]piperidine-3-acetic acid (3RS,4RS) or (3SR,4RS)-4-[3-(R,S)-hydroxy-3-(3-chloro-6-methoxyquinolin-4-yl)propyl]-1-[2-(3,5-difluorophenylthio)ethyl]piperidine-3-acetic acid (3RS,4RS) or (3SR,4RS)-4-[3-(R,S)-hydroxy-3-(3-chloro-6-methoxyquinolin-4-yl)propyl]-1-[2-(2,3,5-trifluorophenylthio)ethyl]piperidine-3-acetic acid (3RS,4RS) or (3SR,4RS)-4-[3-(R,S)-hydroxy-3-(3-chloro-6-methoxyquinolin-4-yl)propyl]-1-[2-(n-propylthio)ethyl]piperidine-3-acetic acid (3RS,4RS) or (3SR,4RS)-4-[3-(R,S)-hydroxy-3-(3-chloro-6-methoxyquinolin-4-yl)propyl]-1-[2-(n-butylthio)ethyl]piperidine-3-acetic acid (3RS,4RS) or (3SR,4RS)-4-[3-(R,S)-hydroxy-3-(3-chloro-6-methoxyquinolin-4-yl)propyl]-1-[2-(cyclopropylthio)ethyl]piperidine-3-acetic acid (3RS,4RS) or (3SR,4RS)-4-[3-(R,S)-hydroxy-3-(3-chloro-6-methoxyquinolin-4-yl)propyl]-1-[2-(cyclobutylthio)ethyl]piperidine-3-acetic acid (3RS,4RS) or (3SR,4RS)-4-[3-(R,S)-hydroxy-3-(3-chloro-6-methoxyquinolin-4-yl)propyl]-1-[2-(cyclopentylthio)ethyl]piperidine-3-acetic acid (3RS,4RS) or (3SR,4RS)-4-[3-(R,S)-hydroxy-3-(3-chloro-6-methoxyquinolin-4-yl)propyl]-1-[2-(cyclohexylthio)ethyl]piperidine-3-acetic acid (3RS,4RS) or (3SR,4RS)-4-[3-(R,S)-hydroxy-3-(3-chloro-6-methoxyquinolin-4-yl)propyl]-1-[2-(thien-2-yl)thioethyl]piperidine-3-acetic acid (3RS,4RS) or (3SR,4RS)-4-[3-(R,S)-hydroxy-3-(3-chloro-6-methoxyquinolin-4-yl)propyl]-1-[2-(5-fluorothien-2-yl)thioethyl]piperidine-3-acetic acid (3RS,4RS) or (3SR,4RS)-4-[3-(R,S)-hydroxy-3-(3-chloro-6-methoxyquinolin-4-yl)propyl]-1-[2-(4-fluorothien-2-yl)thioethyl]piperidine-3-acetic acid (3RS,4RS) or (3SR,4RS)-4-[3-(R,S)-hydroxy-3-(3-chloro-6-methoxyquinolin-4-yl)propyl]-1-[2-(3-fluorothien-2-yl)thioethyl]piperidine-3-acetic acid (3RS,4RS) or (3SR,4RS)-4-[3-(R,S)-hydroxy-3-(3-chloro-6-methoxyquinolin-4-yl)propyl]-1-[2-(thien-3-yl)thioethyl]piperidine-3-acetic acid (3RS,4RS) or (3SR,4RS)-4-[3-(R,S)-hydroxy-3-(3-chloro-6-methoxyquinolin-4-yl)propyl]-1-[2-(1,3-thiazol-2-yl)thioethyl]piperidine-3-acetic acid (3RS,4RS) or (3SR,4RS)-4-[3-(R,S)-hydroxy-3-(3-chloro-6-methoxyquinolin-4-yl)propyl]-1-[2-(pyridin-2-yl)thioethyl]piperidine-3-acetic acid (3RS,4RS) or (3SR,4RS)-4-[3-(R,S)-hydroxy-3-(3-chloro-6-methoxyquinolin-4-yl)propyl]-1-[2-(4-fluoropyridin-2-yl)thioethyl]piperidine-3-acetic acid (3RS,4RS) or (3SR,4RS)-4-[3-(R,S)-hydroxy-3-(3-chloro-6-methoxyquinolin-4-yl)propyl]-1-[2-(3-fluoropyridin-2-yl)thioethyl]piperidine-3-acetic acid (3RS,4RS) or (3SR,4RS)-4-[3-(R,S)-hydroxy-3-(3-chloro-6-methoxyquinolin-4-yl)propyl]-1-[3-(3-fluorophenyl)prop-2-ynyl]piperidine-3-acetic acid (3RS,4RS) or (3SR,4RS)-4-[3-(R,S)-hydroxy-3-(3-chloro-6-methoxyquinolin-4-yl)propyl]-1-[3-(2,5-difluorophenyl)prop-2-ynyl]piperidine-3-acetic acid (3RS,4RS) or (3SR,4RS)-4-[3-(R,S)-hydroxy-3-(3-chloro-6-methoxyquinolin-4-yl)propyl]-1-[3-(3,5-difluorophenyl)prop-2-ynyl]piperidine-3-acetic acid (3RS,4RS) or (3SR,4RS)-4-[3-(R,S)-hydroxy-3-(3-chloro-6-methoxyquinolin-4-yl)propyl]-1-[3-(2,3,5-trifluorophenyl)prop-2-ynyl]piperidine-3-acetic acid (3RS,4RS) or (3SR,4RS)-4-[3-(R,S)-hydroxy-3-(3-chloro-6-methoxyquinolin-4-yl)propyl]-1-[3-(thien-2-yl)prop-2-ynyl]piperidine-3-acetic acid (3RS,4RS) or (3SR,4RS)-4-[3-(R,S)-hydroxy-3-(3-chloro-6-methoxyquinolin-4-yl)propyl]-1-[3-(5-fluorothien-2-yl)prop-2-ynyl]piperidine-3-acetic acid (3RS,4RS) or (3SR,4RS)-4-[3-(R,S)-hydroxy-3-(3-chloro-6-methoxyquinolin-4-yl)propyl]-1-[3-(4-fluorothien-2-yl)prop-2-ynyl]piperidine-3-acetic acid (3RS,4RS) or (3SR,4RS)-4-[3-(R,S)-hydroxy-3-(3-chloro-6-methoxyquinolin-4-yl)propyl]-1-[3-(3-fluorothien-2-yl)prop-2-ynyl]piperidine-3-acetic acid (3RS,4RS) or (3SR,4RS)-4-[3-(R,S)-hydroxy-3-(3-chloro-6-methoxyquinolin-4-yl)propyl]-1-[3-(thien-3-yl)prop-2-ynyl]piperidine-3-acetic acid (3RS,4RS) or (3SR,4RS)-4-[3-(R,S)-fluoro-3-(3-chloro-6-methoxyquinolin-4-yl)propyl]-1-(2-phenylthioethyl)piperidine-3-acetic acid (3RS,4RS) or (3SR,4RS)-4-[3-(R,S)-fluoro-3-(3-chloro-6-methoxyquinolin-4-yl)propyl]-1-[2-(3-fluorophenylthio)ethyl]piperidine-3-acetic acid (3RS,4RS) or (3SR,4RS)-4-[3-(R,S)-fluoro-3-(3-chloro-6-methoxyquinolin-4-yl)propyl]-1-[2-(2,5-difluorophenylthio)ethyl]piperidine-3-acetic acid (3RS,4RS) or (3SR,4RS)-4-[3-(R,S)-fluoro-3-(3-chloro-6-methoxyquinolin-4-yl)propyl]-1-[2-(3,5-difluorophenylthio)-ethyl]piperidine-3-acetic acid (3RS,4RS) or (3SR,4RS)-4-[3-(R,S)-fluoro-3-(3-chloro-6-methoxyquinolin-4-yl)propyl]-1-[2-(2,3,5-trifluorophenylthio)-ethyl]piperidine-3-acetic acid (3RS,4RS) or (3SR,4RS)-4-[3-(R,S)-fluoro-3-(3-chloro-6-methoxyquinolin-4-yl)propyl]-1-[2-(n-propylthio)ethyl]piperidine-3-acetic acid (3RS,4RS) or (3SR,4RS)-4-[3-(R,S)-fluoro-3-(3-chloro-6-methoxyquinolin-4-yl)propyl]-1-[2-(n-butylthio)ethyl]piperidine-3-acetic acid (3RS,4RS) or (3SR,4RS)-4-[3-(R,S)-fluoro-3-(3-chloro-6-methoxyquinolin-4-yl)propyl]-1-[2-(cyclopropylthio)ethyl]piperidine-3-acetic acid (3RS,4RS) or (3SR,4RS)-4-[3-(R,S)-fluoro-3-(3-chloro-6-methoxyquinolin-4-yl)propyl]-1-[2-(cyclobutylthio)ethyl]piperidine-3-acetic acid (3RS,4RS) or (3SR,4RS)-4-[3-(R,S)-fluoro-3-(3-chloro-6-methoxyquinolin-4-yl)propyl]-1-[2-(cyclopentylthio)ethyl]piperidine-3-acetic acid (3RS,4RS) or (3SR,4RS)-4-[3-(R,S)-fluoro-3-(3-chloro-6-methoxyquinolin-4-yl)propyl]-1-[2-(cyclohexylthio)ethyl]piperidine-3-acetic acid (3RS,4RS) or (3SR,4RS)-4-[3-(R,S)-fluoro-3-(3-chloro-6-methoxyquinolin-4-yl)propyl]-1-[2-(thien-2-yl)thioethyl]piperidine-3-acetic acid (3RS,4RS) or (3SR,4RS)-4-[3-(R,S)-fluoro-3-(3-chloro-6-methoxyquinolin-4-yl)propyl]-1-[2-(5-fluorothien-2-yl)-thioethyl]piperidine-3-acetic acid (3RS,4RS) or (3SR,4RS)-4-[3-(R,S)-fluoro-3-(3-chloro-6-methoxyquinolin-4-yl)propyl]-1-[2-(4-fluorothien-2-yl)thioethyl]piperidine-3-acetic acid (3RS,4RS) or (3SR,4RS)-4-[3-(R,S)-fluoro-3-(3-chloro-6-methoxyquinolin-4-yl)propyl]-1-[2-(3-fluorothien-2-yl)thioethyl]piperidine-3-acetic acid (3RS,4RS) or (3SR,4RS)-4-[3-(R,S)-fluoro-3-(3-chloro-6-methoxyquinolin-4-yl)propyl]-1-[2-(thien-3-yl)thioethyl]piperidine-3-acetic acid (3RS,4RS) or (3SR,4RS)-4-[3-(R,S)-fluoro-3-(3-chloro-6-methoxyquinolin-4-yl)propyl]-1-[2-(1,3-thiazol-2-yl)thioethyl]piperidine-3-acetic acid (3RS,4RS) or (3SR,4RS)-4-[3-(R,S)-fluoro-3-(3-chloro-6-methoxyquinolin-4-yl)propyl]-1-[2-(pyridin-2-yl)thioethyl]piperidine-3-acetic acid
(3RS,4RS) or (3SR,4RS)-4-[3-(R,S)-fluoro-3-(3-chloro-6-methoxyquinolin-4-yl)propyl]-1-[2-(4-fluoropyridin-2-yl)thioethyl]piperidine-3-acetic acid
(3RS,4RS) or (3SR,4RS)-4-[3-(R,S)-fluoro-3-(3-chloro-6-methoxyquinolin-4-yl)propyl]-1-[2-(3-fluoropyridin-2-yl)thioethyl]piperidine-3-acetic acid
(3RS,4RS) or (3SR,4RS)-4-[3-(R,S)-fluoro-3-(3-chloro-6-methoxyquinolin-4-yl)propyl]-1-[3-(3-fluorophenyl)prop-2-ynyl]piperidine-3-acetic acid
(3RS,4RS) or (3SR,4RS)-4-[3-(R,S)-fluoro-3-(3-chloro-6-methoxyquinolin-4-yl)propyl]-1-[3-(2,5-difluorophenyl)prop-2-ynyl]piperidine-3-acetic acid
(3RS,4RS) or (3SR,4RS)-4-[3-(R,S)-fluoro-3-(3-chloro-6-methoxyquinolin-4-yl)propyl]-1-[3-(3,5-difluorophenyl)prop-2-ynyl]piperidine-3-acetic acid
(3RS,4RS) or (3SR,4RS)-4-[3-(R,S)-fluoro-3-(3-chloro-6-methoxyquinolin-4-yl)propyl]-1-[3-(2,3,5-trifluorophenyl)prop-2-ynyl]piperidine-3-acetic acid
(3RS,4RS) or (3SR,4RS)-4-[3-(R,S)-fluoro-3-(3-chloro-6-methoxyquinolin-4-yl)propyl]-1-[3-(thien-2-yl)prop-2-ynyl]piperidine-3-acetic acid
(3RS,4RS) or (3SR,4RS)-4-[3-(R,S)-fluoro-3-(3-chloro-6-methoxyquinolin-4-yl)propyl]-1-[3-(5-fluorothien-2-yl)prop-2-ynyl]piperidine-3-acetic acid
(3RS,4RS) or (3SR,4RS)-4-[3-(R,S)-fluoro-3-(3-chloro-6-methoxyquinolin-4-yl)propyl]-1-[3-(4-fluorothien-2-yl)prop-2-ynyl]piperidine-3-acetic acid
(3RS,4RS) or (3SR,4RS)-4-[3-(R,S)-fluoro-3-(3-chloro-6-methoxyquinolin-4-yl)propyl]-1-[3-(3-fluorothien-2-yl)prop-2-ynyl]piperidine-3-acetic acid
(3RS,4RS) or (3SR,4RS)-4-[3-(R,S)-fluoro-3-(3-chloro-6-methoxyquinolin-4-yl)propyl]-1-[3-(thien-3-yl)prop-2-ynyl]piperidine-3-acetic acid
(3RS,4RS) or (3SR,4RS)-4-[3-(R,S)-amino-3-(3-chloro-6-methoxyquinolin-4-yl)propyl]-1-(2-phenylthioethyl)piperidine-3-acetic acid
(3RS,4RS) or (3SR,4RS)-4-[3-(R,S)-amino-3-(3-chloro-6-methoxyquinolin-4-yl)propyl]-1-[2-(3-fluorophenylthio)ethyl]piperidine-3-acetic acid
(3RS,4RS) or (3SR,4RS)-4-[3-(R,S)-amino-3-(3-chloro-6-methoxyquinolin-4-yl)propyl]-1-[2-(2,5-difluorophenylthio)ethyl]piperidine-3-acetic acid
(3RS,4RS) or (3SR,4RS)-4-[3-(R,S)-amino-3-(3-chloro-6-methoxyquinolin-4-yl)propyl]-1-[2-(3,5-difluorophenylthio)ethyl]piperidine-3-acetic acid
(3RS,4RS) or (3SR,4RS)-4-[3-(R,S)-amino-3-(3-chloro-6-methoxyquinolin-4-yl)propyl]-1-[2-(2,3,5-trifluorophenylthio)ethyl]piperidine-3-acetic acid
(3RS,4RS) or (3SR,4RS)-4-[3-(R,S)-amino-3-(3-chloro-6-methoxyquinolin-4-yl)propyl]-1-[2-(n-propylthio)ethyl]piperidine-3-acetic acid
(3RS,4RS) or (3SR,4RS)-4-[3-(R,S)-amino-3-(3-chloro-6-methoxyquinolin-4-yl)propyl]-1-[2-(n-butylthio)ethyl]piperidine-3-acetic acid
(3RS,4RS) or (3SR,4RS)-4-[3-(R,S)-amino-3-(3-chloro-6-methoxyquinolin-4-yl)propyl]-1-[2-(cyclopropylthio)ethyl]piperidine-3-acetic acid
(3RS,4RS) or (3SR,4RS)-4-[3-(R,S)-amino-3-(3-chloro-6-methoxyquinolin-4-yl)propyl]-1-[2-(cyclobutylthio)ethyl]piperidine-3-acetic acid
(3RS,4RS) or (3SR,4RS)-4-[3-(R,S)-amino-3-(3-chloro-6-methoxyquinolin-4-yl)propyl]-1-[2-(cyclopentylthio)ethyl]piperidine-3-acetic acid
(3RS,4RS) or (3SR,4RS)-4-[3-(R,S)-amino-3-(3-chloro-6-methoxyquinolin-4-yl)propyl]-1-[2-(cyclohexylthio)ethyl]piperidine-3-acetic acid
(3RS,4RS) or (3SR,4RS)-4-[3-(R,S)-amino-3-(3-chloro-6-methoxyquinolin-4-yl)propyl]-1-[2-(thien-2-yl)thioethyl]piperidine-3-acetic acid
(3RS,4RS) or (3SR,4RS)-4-[3-(R,S)-amino-3-(3-chloro-6-methoxyquinolin-4-yl)propyl]-1-[2-(5-fluorothien-2-yl)thioethyl]piperidine-3-acetic acid
(3RS,4RS) or (3SR,4RS)-4-[3-(R,S)-amino-3-(3-chloro-6-methoxyquinolin-4-yl)propyl]-1-[2-(4-fluorothien-2-yl)-thioethyl]piperidine-3-acetic acid
(3RS,4RS) or (3SR,4RS)-4-[3-(R,S)-amino-3-(3-chloro-6-methoxyquinolin-4-yl)propyl]-1-[2-(3-fluorothien-2-yl)-thioethyl]piperidine-3-acetic acid
(3RS,4RS) or (3SR,4RS)-4-[3-(R,S)-amino-3-(3-chloro-6-methoxyquinolin-4-yl)propyl]-1-[2-(thien-3-yl)thioethyl]piperidine-3-acetic acid
(3RS,4RS) or (3SR,4RS)-4-[3-(R,S)-amino-3-(3-chloro-6-methoxyquinolin-4-yl)propyl]-1-[2-(1,3-thiazol-2-yl)thioethyl]piperidine-3-acetic acid
(3RS,4RS) or (3SR,4RS)-4-[3-(R,S)-amino-3-(3-chloro-6-methoxyquinolin-4-yl)propyl]-1-[2-(pyridin-2-yl)thioethyl]piperidine-3-acetic acid
(3RS,4RS) or (3SR,4RS)-4-[3-(R,S)-amino-3-(3-chloro-6-methoxyquinolin-4-yl)propyl]-1-[2-(4-fluoropyridin-2-yl)thioethyl]piperidine-3-acetic acid
(3RS,4RS) or (3SR,4RS)-4-[3-(R,S)-amino-3-(3-chloro-6-methoxyquinolin-4-yl)propyl]-1-[2-(3-fluoropyridin-2-yl)thioethyl]piperidine-3-acetic acid
(3RS,4RS) or (3SR,4RS)-4-[3-(R,S)-amino-3-(3-chloro-6-methoxyquinolin-4-yl)propyl]-1-[3-(3-fluorophenyl)prop-2-ynyl]piperidine-3-acetic acid
(3RS,4RS) or (3SR,4RS)-4-[3-(R,S)-amino-3-(3-chloro-6-methoxyquinolin-4-yl)propyl]-1-[3-(2,5-difluorophenyl)prop-2-ynyl]piperidine-3-acetic acid
(3RS,4RS) or (3SR,4RS)-4-[3-(R,S)-amino-3-(3-chloro-6-methoxyquinolin-4-yl)propyl]-1-[3-(3,5-difluorophenyl)prop-2-ynyl]piperidine-3-acetic acid
(3RS,4RS) or (3SR,4RS)-4-[3-(R,S)-amino-3-(3-chloro-6-methoxyquinolin-4-yl)propyl]-1-[3-(2,3,5-trifluorophenyl)prop-2-ynyl]piperidine-3-acetic acid
(3RS,4RS) or (3SR,4RS)-4-[3-(R,S)-amino-3-(3-chloro-6-methoxyquinolin-4-yl)propyl]-1-[3-(thien-2-yl)prop-2-ynyl]piperidine-3-acetic acid
(3RS,4RS) or (3SR,4RS)-4-[3-(R,S)-amino-3-(3-chloro-6-methoxyquinolin-4-yl)propyl]-1-[3-(5-fluorothien-2-yl)prop-2-ynyl]piperidine-3-acetic acid
(3RS,4RS) or (3SR,4RS)-4-[3-(R,S)-amino-3-(3-chloro-6-methoxyquinolin-4-yl)propyl]-1-[3-(4-fluorothien-2-yl)prop-2-ynyl]piperidine-3-acetic acid
(3RS,4RS) or (3SR,4RS)-4-[3-(R,S)-amino-3-(3-chloro-6-methoxyquinolin-4-yl)propyl]-1-[3-(3-fluorothien-2-yl)prop-2-ynyl]piperidine-3-acetic acid
(3RS,4RS) or (3SR,4RS)-4-[3-(R,S)-amino-3-(3-chloro-6-methoxyquinolin-4-yl)propyl]-1-[3-(thien-3-yl)prop-2-ynyl]piperidine-3-acetic acid
(3RS,4RS) or (3SR,4RS)-4-[3-oxo-3-(3-chloro-6-methoxyquinolin-4-yl)propyl]-1-(2-phenylthioethyl)piperidine-3-acetic acid
(3RS,4RS) or (3SR,4RS)-4-[3-oxo-3-(3-chloro-6-methoxyquinolin-4-yl)propyl]-1-[2-(3-fluorophenylthio)-ethyl]piperidine-3-acetic acid
(3RS,4RS) or (3SR,4RS)-4-[3-oxo-3-(3-chloro-6-methoxyquinolin-4-yl)propyl]-1-[2-(2,5-difluorophenylthio)ethyl]piperidine-3-acetic acid
(3RS,4RS) or (3SR,4RS)-4-[3-oxo-3-(3-chloro-6-methoxyquinolin-4-yl)propyl]-1-[2-(3,5-difluorophenylthio)ethyl]piperidine-3-acetic acid
(3RS,4RS) or (3SR,4RS)-4-[3-oxo-3-(3-chloro-6-methoxyquinolin-4-yl)propyl]-1-[2-(2,3,5-trifluorophenylthio)ethyl]piperidine-3-acetic acid (3RS,4RS) or (3SR,4RS)-4-[3-oxo-3-(3-chloro-6-methoxyquinolin-4-yl)propyl]-1-[2-(n-propylthio)ethyl]piperidine-3-acetic acid
(3RS,4RS) or (3SR,4RS)-4-[3-oxo-3-(3-chloro-6-methoxyquinolin-4-yl)propyl]-1-[2-(n-butylthio)ethyl]piperidine-3-acetic acid
(3RS,4RS) or (3SR,4RS)-4-[3-oxo-3-(3-chloro-6-methoxyquinolin-4-yl)propyl]-1-[2-(cyclopropylthio)ethyl]piperidine-3-acetic acid
(3RS,4RS) or (3SR,4RS)-4-[3-oxo-3-(3-chloro-6-methoxyquinolin-4-yl)propyl]-1-[2-(cyclobutylthio)ethyl]piperidine-3-acetic acid
(3RS,4RS) or (3SR,4RS)-4-[3-oxo-3-(3-chloro-6-methoxyquinolin-4-yl)propyl]-1-[2-(cyclopentylthio)ethyl]piperidine-3-acetic acid
(3RS,4RS) or (3SR,4RS)-4-[3-oxo-3-(3-chloro-6-methoxyquinolin-4-yl)propyl]-1-[2-(cyclohexylthio)ethyl]piperidine-3-acetic acid
(3RS,4RS) or (3SR,4RS)-4-[3-oxo-3-(3-chloro-6-methoxyquinolin-4-yl)propyl]-1-[2-(thien-2-yl)thioethyl]piperidine-3-acetic acid
(3RS,4RS) or (3SR,4RS)-4-[3-oxo-3-(3-chloro-6-methoxyquinolin-4-yl)propyl]-1-[2-(5-fluorothien-2-yl)thioethyl]piperidine-3-acetic acid
(3RS,4RS) or (3SR,4RS)-4-[3-oxo-3-(3-chloro-6-methoxyquinolin-4-yl)propyl]-1-[2-(4-fluorothien-2-yl)thioethyl]piperidine-3-acetic acid
(3RS,4RS) or (3SR,4RS)-4-[3-oxo-3-(3-chloro-6-methoxyquinolin-4-yl)propyl]-1-[2-(3-fluorothien-2-yl)thioethyl]piperidine-3-acetic acid
(3RS,4RS) or (3SR,4RS)-4-[3-oxo-3-(3-chloro-6-methoxyquinolin-4-yl)propyl]-1-[2-(thien-3-yl)thioethyl]piperidine-3-acetic acid
(3RS,4RS) or (3SR,4RS)-4-[3-oxo-3-(3-chloro-6-methoxyquinolin-4-yl)propyl]-1-[2-(1,3-thiazol-2-yl)thioethyl]piperidine-3-acetic acid
(3RS,4RS) or (3SR,4RS)-4-[3-oxo-3-(3-chloro-6-methoxyquinolin-4-yl)propyl]-1-[2-(pyridin-2-yl)thioethyl]piperidine-3-acetic acid
(3RS,4RS) or (3SR,4RS)-4-[3-oxo-3-(3-chloro-6-methoxyquinolin-4-yl)propyl]-1-[2-(4-fluoropyridin-2-yl)thioethyl]piperidine-3-acetic acid
(3RS,4RS) or (3SR,4RS)-4-[3-oxo-3-(3-chloro-6-methoxyquinolin-4-yl)propyl]-1-[2-(3-fluoropyridin-2-yl)thioethyl]piperidine-3-acetic acid
(3RS,4RS) or (3SR,4RS)-4-[3-oxo-3-(3-chloro-6-methoxyquinolin-4-yl)propyl]-1-[3-(3-fluorophenyl)prop-2-ynyl]piperidine-3-acetic acid
(3RS,4RS) or (3SR,4RS)-4-[3-oxo-3-(3-chloro-6-methoxyquinolin-4-yl)propyl]-1-[3-(2,5-difluorophenyl)prop-2-ynyl]piperidine-3-acetic acid
(3RS,4RS) or (3SR,4RS)-4-[3-oxo-3-(3-chloro-6-methoxyquinolin-4-yl)propyl]-1-[3-(3,5-difluorophenyl)prop-2-ynyl]piperidine-3-acetic acid
(3RS,4RS) or (3SR,4RS)-4-[3-oxo-3-(3-chloro-6-methoxyquinolin-4-yl)propyl]-1-[3-(2,3,5-trifluorophenyl)prop-2-ynyl]piperidine-3-acetic acid
(3RS,4RS) or (3SR,4RS)-4-[3-oxo-3-(3-chloro-6-methoxyquinolin-4-yl)propyl]-1-[3-(thien-2-yl)prop-2-ynyl]piperidine-3-acetic acid
(3RS,4RS) or (3SR,4RS)-4-[3-oxo-3-(3-chloro-6-methoxyquinolin-4-yl)propyl]-1-[3-(5-fluorothien-2-yl)prop-2-ynyl]piperidine-3-acetic acid
(3RS,4RS) or (3SR,4RS)-4-[3-oxo-3-(3-chloro-6-methoxyquinolin-4-yl)propyl]-1-[3-(4-fluorothien-2-yl)prop-2-ynyl]piperidine-3-acetic acid
(3RS,4RS) or (3SR,4RS)-4-[3-oxo-3-(3-chloro-6-methoxyquinolin-4-yl)propyl]-1-[3-(3-fluorothien-2-yl)prop-2-ynyl]piperidine-3-acetic acid
(3RS,4RS) or (3SR,4RS)-4-[3-oxo-3-(3-chloro-6-methoxyquinolin-4-yl)propyl]-1-[3-(thien-3-yl)prop-2-ynyl]piperidine-3-acetic acid

EXAMPLE 1

Synthesis of the 4 Stereoisomers of (3RS,4RS)-4-[3-(R,S)-hydroxy-3-(3-chloro-6-methoxyquinolin-4-yl)propyl]-1-[2-(2,5-difluorophenylsulfanyl)ethyl]piperidine-3-carboxylic acid (3R,4R)-4-[3-(R)-hydroxy-3-(3-chloro-6-methoxyquinolin-4-yl]propyl]-1-[2-(2,5-difluorophenylsulfanyl)ethyl]piperidine-3-carboxylic acid
(3R,4R)-4-[3-(S)-hydroxy-3-(3-chloro-6-methoxyquinolin-4-yl]propyl]-1-[2-(2,5-difluorophenylsulfanyl)ethyl]piperidine-3-carboxylic acid
(3S,4S)-4-[3-(S)-hydroxy-3-(3-chloro-6-methoxyquinolin-4-yl]propyl]-1-[2-(2,5-difluorophenylsulfanyl)ethyl]piperidine-3-carboxylic acid
(3S,4S)-4-[3-(R)-hydroxy-3-(3-chloro-6-methoxyquinolin-4-yl]propyl]-1-[2-(2,5-difluorophenylsulfanyl)ethyl]piperidine-3-carboxylic acid The four stereoisomers are hereinafter referred to as A, B, C and D. Their absolute stereochemistries are not known.
Stereoisomer A:
2 cm$^3$ of a 1 N aqueous sodium hydroxide solution are added to 390 mg of methyl 4-[3-hydroxy-3-(3-chloro-6-methoxyquinolin-4-yl)propyl]-1-[2-(2,5-difluorophenylsulfanyl)ethyl]piperidine-3-carboxylate (ester isomer A) in 10 cm$^3$ of dioxane. The reaction medium is then heated at 70° C. for 5 hours, is allowed to return to 20° C. for 18 hours and is then reheated at 70° C. for 2 hours. After returning to 20° C., the reaction medium is evaporated under reduced pressure (2 kPa; 45° C.). The residue is taken up in 25 cm$^3$ of distilled water and extracted with 25 cm$^3$ of diethyl ether. The aqueous phase is acidified with 1.9 cm$^3$ of a 1 N aqueous hydrochloric acid solution and is extracted with 3 times 70 cm$^3$ of ethyl acetate. The organic phase is dried over magnesium sulfate, filtered through a sintered glass funnel, and then concentrated under reduced pressure. (2 kPa; 45° C.). The residue is taken up with 25 cm$^3$ of acetone and then reconcentrated under reduced pressure (2 kPa; 45° C.). After drying in an incubator under reduced pressure (10 kPa; 20° C.), 340 mg of 4-[3-hydroxy-3-(3-chloro-6-methoxyquinolin-4-yl)propyl]-1-[2-(2,5-difluorophenylsulfanyl)ethyl]piperidine-3-carboxylic acid (isomer A), in the base of a beige solid, are obtained.
$^1$H-NMR spectrum (400 MHz, (CD$_3$)$_2$SO d6, δ in ppm): 1.34 (mt: 1H); from 1.50 to 1.85 (mt: 5H); 2.10 (mt: 1H); 2.28 (mt: 1H); 2.43 (very broad d, J=11.5 Hz: 1H); from 2.45 to 2.60 (mt: 1H); 2.65 (t, J=7 Hz: 2H); 2.73 (unresolved peak: 1H); 2.86 (mf: 1H); 3.18 (mt: 2H); 3.90 (s: 3H); 5.47 (dd, J=9 and 5 Hz: 1H); 6.03 (mf: 1H); 7.08 (mt: 1H); 7.27 (mt: 1H); 7.34 (mt: 1H); 7.44 (dd, J=9 and 3 Hz: 1H); 7.95 (d, J=9 Hz: 1H); 8.21 (d, J=3 Hz: 1H); 8.65 (s: 1H).
$\alpha_D^{20}$=52.3°+/−1.1 in 0.5% methanol.
Stereoisomer B:
2.4 cm$^3$ of a 1 N aqueous sodium hydroxide solution are added to 460 mg of methyl 4-[3-hydroxy-3-(3-chloro-6-methoxyquinolin-4-yl)propyl]-1-[2-(2,5-difluorophenylsulfanyl)ethyl]piperidine-3-carboxylate (ester isomer B) in 10 cm$^3$ of dioxane. The reaction medium is then heated at 70° C. for 5 hours, left to return to 20° C. for 18 hours, and then heated again at 70° C. for 2 hours. After returning to 20° C., the reaction medium is evaporated under reduced pressure (2 kPa; 45° C.). The residue is taken up in 25 cm³ of distilled water and is extracted with 25 cm³ of diethyl ether. The aqueous phase is acidified (pH=6) with 2.3 cm³ of a 1 N aqueous hydrochloric acid solution and is extracted with 3 times 70 cm³ ethyl acetate. The organic phase is dried over magnesium sulfate, filtered through a sintered glass funnel, and then concentrated under reduced pressure (2 kPa; 45° C.). The residue is taken up with 25 cm³ of acetone, and then reconcentrated under reduced pressure (2 kPa; 45° C.). After drying in an oven under reduced pressure (10 kPa; 20° C.), 310 mg of 4-[3-hydroxy-3-(3-chloro-6-methoxyquinolin-4-yl)propyl]-1-[2-(2,5-difluorophenylsulfanyl)ethyl]piperidine-3-carboxylic acid (isomer B), in the form of a pale yellow solid, are obtained.

¹H-NMR spectrum (400 MHz, (CD₃)₂SO d6 at a temperature of 303 K, δ in ppm): from 1.20 to 1.40 (mt: 1H); from 1.50 to 1.85 (mt: 5H); from 2.00 to 2.15 (mt: 1H); from 2.20 to 2.55 (broad unresolved peak: 2H); 2.60 (mt: 1H); from 2.60 to 3.05 (mt: 4H); 3.22 (mt: 2H); 3.90 (s: 3H); 5.46 (mt: 1H); 6.01 (d, J=3.5 Hz: 1H); 7.10 (mt: 1H); 7.29 (mt: 1H); 7.36 (mt: 1H); 7.44 (dd, J=9 and 3 Hz: 1H); 7.95 (d, J=9 Hz: 1H); 8.21 (d, J=3 Hz: 1H); 8.65 (s: 1H).

$\alpha_D^{20}$=-53.1°+/-1.1 in 0.5% methanol.

Stereoisomer C:

1.4 cm³ of a 1 N aqueous sodium hydroxide solution are added to 270 mg of methyl 4-[3-hydroxy-3-(3-chloro-6-methoxyquinolin-4-yl)propyl]-1-[2-(2,5-difluorophenylsulfanyl)ethyl]piperidine-3-carboxylate (ester isomer C) in 10 cm³ of dioxane. The reaction medium is then heated at 70° C. for 5 hours, allowed to return to 20° C. for 18 hours, and then heated again at 70° C. for 4 hours. After returning to 20° C., the reaction medium is evaporated under reduced pressure (2 kPa; 45° C.). The residue is taken up in 25 cm³ of distilled water and extracted with 25 cm³ of diethyl ether. The aqueous phase is acidified (pH=6) with 1.3 cm³ of a 1 N aqueous hydrochloric acid solution and is extracted with 3 times 70 cm³ of ethyl acetate. The organic phase is dried over magnesium sulfate, filtered through a sintered glass funnel, and then concentrated under reduced pressure (2 kPa; 45° C.). The residue is taken up with 25 cm³ of acetone, and then reconcentrated under reduced pressure (2 kPa; 45° C.). After drying in an incubator under reduced pressure (10 kPa; 20° C.), 310 mg of 4-[3-hydroxy-3-(3-chloro-6-methoxyquinolin-4-yl)propyl]-1-[2-(2,5-difluorophenylsulfanyl)ethyl]piperidine-3-carboxylic acid (isomer C), in the form of a beige solid, are obtained.

¹H-NMR spectrum (300 MHz, (CD₃)₂SO d6, δ in ppm): from 1.20 to 1.40 (mt: 1H); from 1.45 to 1.90 (mt: 5H); from 2.05 to 2.30 (mt: 2H); 2.39 (very broad d, J=10.5 Hz: 1H); 2.56 (mt: 1H); 2.64 (t, J=7 Hz: 2H); from 2.65 to 2.80 (unresolved peak: 1H); 2.92 (mt: 1H); 3.17 (mt: 2H); 3.90 (s: 3H); 5.45 (dd, J=8.5 and 5 Hz: 1H); 6.01 (unresolved peak: 1H); 7.08 (mt: 1H); from 7.20 to 7.40 (mt: 2H); 7.43 (dd, J=9 and 3 Hz: 1H); 7.94 (d, J=9 Hz: 1H); 8.22 (d, J=3 Hz: 1H); 8.64 (s: 1H).

$\alpha_D^{20}$=60.1°+/-1.2 in 0.5% methanol.

Stereoisomer D:

1.4 cm³ of a 1 N aqueous sodium hydroxide solution are added to 270 mg of methyl 4-[3-hydroxy-3-(3-chloro-6-methoxyquinolin-4-yl)propyl]-1-[2-(2,5-difluorophenylsulfanyl)ethyl]piperidine-3-carboxylate (ester isomer D) in 10 cm³ of dioxane. The reaction medium is then heated at 70° C. for 5 hours, allowed to return to 20° C. for 18 hours, and then heated again at 70° C. for 4 hours. After returning to 20° C., the reaction medium is evaporated under reduced pressure (2 kPa; 45° C.). The residue is taken up in 25 cm³ of distilled water and extracted with 25 cm³ of diethyl ether. The aqueous phase is acidified (pH=6) with 1.3 cm³ of a 1 N aqueous hydrochloric acid solution and is extracted with 3 times 70 cm³ of ethyl acetate. The organic phase is dried over magnesium sulfate, filtered through a sintered glass funnel, and then concentrated under reduced pressure (2 kPa; 45° C.). The residue is taken up with 25 cm³ of acetone, and then reconcentrated under reduced pressure (2 kPa; 45° C.). After drying in an incubator under reduced pressure (10 kPa; 20° C.), 200 mg of 4-[3-hydroxy-3-(3-chloro-6-methoxyquinolin-4-yl)propyl]-1-[2-(2,5-difluorophenylsulfanyl)ethyl]piperidine-3-carboxylic acid (isomer D), in the form of a white solid, are obtained.

¹H-NMR spectrum (300 MHz, (CD₃)₂SO d6, δ in ppm): from 1.20 to 1.40 (mt: 1H); from 1.45 to 1.85 (mt: 5H); from 2.05 to 2.30 (mt: 2H); 2.39 (very broad d, J=10.5 Hz: 1H); 2.56 (mt: 1H); from 2.60 to 2.80 (unresolved peak: 1H); 2.64 (t, J=7 Hz: 2H); 2.91 (mt: 1H); 3.17 (mt: 2H); 3.90 (s: 3H); 5.45 (dd, J=8.5 and 5 Hz: 1H); 6.01 (unresolved peak: 1H); 7.08 (mt: 1H); from 7.20 to 7.40 (mt: 2H); 7.43 (dd, J=9 and 3 Hz: 1H); 7.94 (d, J=9 Hz: 1H); 8.22 (d, J=3 Hz: 1H); 8.64 (s: 1H).

$\alpha_D^{20}$=-60.1°+/-1.2 in 0.5% methanol.

Methyl (3RS,4RS)-4-[3-(R,S)-hydroxy-3-(3-chloro-6-methoxyquinolin-4-yl)propyl]-1-[2-(2,5-difluorophenylsulfanyl)ethyl]piperidine-3-carboxylate Methyl (3R,4R)-4-[3-(R)-hydroxy-3-(3-chloro-6-methoxyquinolin-4-yl)propyl]-1-[2-(2,5-difluorophenylsulfanyl)ethyl]piperidine-3-carboxylate Methyl (3S,4S)-4-[3-(S)-hydroxy-3-(3-chloro-6-methoxyquinolin-4-yl)propyl]-1-[2-(2,5-difluorophenylsulfanyl)ethyl]piperidine-3-carboxylate Methyl (3S,4S)-4-[3-(R,)-hydroxy-3-(3-chloro-6-methoxyquinolin-4-yl)propyl]-1-[2-(2,5-difluorophenylsulfanyl)ethyl]piperidine-3-carboxylate Methyl (3S,4S)-4-[3-(S,)-hydroxy-3-(3-chloro-6-methoxyquinolin-4-yl)propyl]-1-(2-(2,5-difluorophenylsulfanyl)ethyl]piperidine-3-carboxylate.

The four stereoisomers are hereinafter referred to as A, B, C, and D. Their absolute stereochemistries are not known.

1.5 cm³ of triethylamine, 2.15 g of potassium carbonate and 0.85 g of potassium iodide are added to 2.35 g of methyl (3RS,4RS)-4-[3-(R,S)-hydroxy-(3-chloro-6-methoxyquinolin-4-yl)propyl]piperidine-3-carboxylate hydrochloride solubilized in 110 cm³ of acetonitrile. 1.3 g of 1-(2-bromoethylsulfanyl)-2,5-difluoro)benzene are then added. The reaction medium is brought to 60° C. for 16 hours. Next, the medium is allowed to return to 20° C., it is filtered through a sintered glass funnel No. 3, and washing is then carried out with 2×20 cm³ of acetonitrile, followed by evaporation under reduced pressure (45° C.; 5 kPa). The residue is purified by chromatography, under an argon pressure of 150 kPa, on a column of silica gel (particle size 0.065–0.2 μm; diameter 2.5 cm; height 40 cm), eluting with a mixture of cyclohexane-ethyl acetate (60/40 by volume) and collecting fractions of 50 cm³. Fractions 8 to 16 are pooled, and then concentrated under reduced pressure (45° C.; 5 kPa). 2.15 g of methyl (3RS,4RS)-4-[3-(R,S)-hydroxy-3-(3-chloro-6-methoxyquinolin-4-yl)propyl]-1-[2-(2,5-difluorophenysulfanyl)ethyl]piperidine-3-carboxylate (mixture of isomers A, B, C, D), in the form of a colorless oil, are obtained.

The 1-(2-bromoethylsulfanyl)-(2,5-difluoro)benzene is prepared according to patent application WO 200240474.

¹H-NMR spectrum (300 MHz, (CD₃)₂SO d6, δ in ppm). A diastereoisomer mixture in 50/50 proportions is observed.
* from 1.10 to 1.90 (mt: 6H); from 1.90 to 2.90 (mt: 7H);

2.37 (broad d, J=10.5 Hz: 1H); 3.10 (t, J=7 Hz: 2H); 3.40 and 3.55 (2s: 3H in all); 3.88 and 3.89 (2s: 3H in all); 5.44 (mt: 1H); 6.01 (broad s: 1H); 7.05 (mt: 1H); from 7.20 to 7.35 (mt: 2H); 7.44 (dd, J=9 and 3 Hz: 1H); 7.95 (d, J=9 Hz: 1H); 8.19 (mt: 1H); 8.65 and 8.66 (2s: 1H in all).

Using the mixture of stereoisomers A, B, C, D obtained above, the separation of each stereoisomer is carried by HPLC.

The separation of the 2 pairs of stereoisomers (A+B) and (C+D) is carried out on a C18 Symmetry stationary phase using 2.7 g of the mixture A, B, C, D described above, particle size 7 μmm; diameter 60 mm; mass of the stationary phase 700 g, under a pressure of 500 kPa, the mobile phase is composed of a mixture of methanolaqueous buffer solution (pH=4.9)-acetonitrile (10/30/60 by volume) having a flow rate of 120 cm$^3$ per minute, and the wavelength of the UV detector is set at 280 nm.

The fractions containing the first pair of enantiomers noted (A+B) are pooled and evaporated under reduced pressure (2 kPa) at a temperature in the region of 40° C. The residue obtained is taken up in water and is then extracted twice with dichloromethane. The organic phase is dried over magnesium sulfate, filtered, and then evaporated under reduced pressure (2 kPa; 45° C.). 850 mg of product (mixture A+B) are obtained. The fractions containing the second pair of enantiomers noted (C+D) are pooled and evaporated under reduced pressure (2 kPa) at a temperature in the region of 40° C. The residue obtained is taken up in water and is then extracted twice with dichloromethane. The organic phase is dried over magnesium sulfate, filtered, and evaporated under reduced pressure (2 kPa; 45° C.). 540 mg of product (mixture C+D) are obtained.

Next, the products of the pair of enantiomers (A, B) are separated on a chiralcel OD column (particle size 20 μmm; diameter 80 mm; mass of the stationary phase 1250 g) under a pressure of 1000 kPa, the mobile phase is composed of a mixture of heptane-isopropanol-methanol-triethylamine (90/5/5/0.1 by volume) having a flow rate of 150 cm$^3$ per minute, and the wavelength of the UV detector is set at 280 nm. The fractions containing each product are isolated and then concentrated under reduced pressure (3 kPa) at a temperature in the region of 40° C.; 0.391 g of the enantiomer A and 0.459 g of the enantiomer B are obtained.

Similarly, the products of the pair of enantiomers (C, D) are separated on a chiralpak AD column (particle size 20 μmm; diameter 80 mm; mass of the stationary phase 750 g) under a pressure of 1000 kPa, the mobile phase is composed of a mixture of hexane-isopropanol-methanol-triethylamine (80/10/10/0.1 by volume) having a flow rate of 100 cm$^3$ per minute, and the wavelength of the UV detector is set to 280 nm. The fractions containing each product are isolated and then concentrated under reduced pressure (3 kPa) at a temperature in the region of 40° C.; 0.27 g of the enantiomer C and 0.27 g of the enantiomer D are obtained.

Stereoisomer A $^1$H-NMR spectrum (300 MHz, $(CD_3)_2SO$ d6, δ in ppm): from 1.10 to 1.30 (mt: 1H); 1.50 (mt: 1H); from 1.60 to 1.85 (mt: 4H); 2.08 (mt: 1H); 2.22 (mt: 1H); 2.36 (very broad d, J=10.5 Hz: 1H); from 2.45 to 2.60 (mt: 3H); 2.63 (mt: 1H); 2.75 (mt: 1H); 3.10 (t, J=7 Hz: 2H); 3.40 (s: 3H); 3.88 (s: 3H); 5.44 (mt: 1H); 6.02 (d, J=3.5 Hz: 1H); 7.05 (mt: 1H); from 7.20 to 7.35 (mt: 2H); 7.43 (dd, J=9 and 3 Hz: 1H); 7.95 (d, J=9 Hz: 1H); 8.19 (d, J=3 Hz: 1H); 8.65 (s: 1H).

$α_D^{20}$=40.2°+/−0.9 in 0.5% of DMSO

HPLC conditions: Chiralcel OD column, flow rate 1 cm$^3$/min,

Elution conditions from 0 to 16 min: heptane-isopropanol-ethanol-triethylamine (88/6/6/0.1 by volume)

Retention time: 10.47 min

Stereoisomer B $^1$H-NMR spectrum (300 MHz, $(CD_3)_2SO$ d6, δ in ppm): from 1.10 to 1.30 (mt: 1H); 1.51 (mt: 1H); from 1.60 to 1.85 (mt: 4H); from 2.00 to 2.20 (mt: 1H); 2.23 (mt: 1H); 2.37 (very broad d, J=10.5 Hz: 1H); from 2.45 to 2.60 (mt: 3H); 2.64 (mt: 1H); 2.75 (mt: 1H); 3.11 (t, J=7 Hz: 2H); 3.41 (s: 3H); 3.89 (s: 3H); 5.45 (mt: 1H); 6.03 (d, J=4 Hz: 1H); 7.07 (mt: 1H); from 7.20 to 7.35 (mt: 2H); 7.44 (dd, J=9 and 3 Hz: 1H); 7.95 (d, J=9 Hz: 1H); 8.20 (d, J=3 Hz: 1H); 8.66 (s: 1H).

$α_D^{20}$=−38.3°+/−0.9 in 0.5% DMSO

HPLC conditions: Chiralcel OD column, flow rate 1 cm$^3$/min,

Elution conditions from 0 to 16 min; heptane-isopropanol-ethanol-triethylamine (88/6/6/0.1 by volume)

Retention time: 13.95 min

Stereoisomer C $^1$H-NMR spectrum (300 MHz, $(CD_3)_2SO$ d6, δ in ppm): from 1.30 to 1.55 (mt: 2H); from 1.55 to 1.90 (mt: 4H); 1.97 (mt: 1H); 2.19 (mt: 1H); 2.37 (very broad d, J=10.5 Hz: 1H); from 2.40 to 2.65 (mt: 3H); 2.68 (mt: 1H); 2.80 (mt: 1H); 3.11 (t, J=7 Hz: 2H); 3.55 (s: 3H); 3.90 (s: 3H); 5.45 (mt: 1H); 6.03 (d, J=3.5 Hz: 1H); 7.06 (mt: 1H); from 7.20 to 7.35 (mt: 2H); 7.44 (dd, J=9 and 3 Hz: 1H); 7.96 (d, J=9 Hz: 1H); 8.20 (d, J=3 Hz: 1H); 8.66 (s: 1H).

$α_D^{20}$=26.6°+/−0.8 in 0.5% DMSO

HPLC conditions: Chiralpak AD column, flow rate 1 cm$^3$/min,

Elution conditions from 0 to 20 min: heptane-isopropanol-ethanol-triethylamine (88/5/7/0.1 by volume)

Retention time: 13.01 min

Stereoisomer D $^1$H-NMR spectrum (300 MHz, $(CD_3)_2SO$ d6, δ in ppm): from 1.30 to 1.55 (mt: 2H); from 1.55 to 1.85 (mt: 4H); 1.97 (mt: 1H); 2.18 (mt: 1H); 2.37 (very broad d, J=10.5 Hz: 1H); from 2.40 to 2.65 (mt: 3H); 2.69 (mt: 1H); 2.79 (mt: 1H); 3.11 (t, J=7 Hz: 2H); 3.55 (s: 3H); 3.89 (s: 3H); 5.45 (mt: 1H); 6.03 (d, J=3.5 Hz: 1H); 7.06 (mt: 1H); from 7.20 to 7.35 (mt: 2H); 7.44 (dd, J=9 and 3 Hz: 1H); 7.96 (d, J=9 Hz: 1H); 8.21 (d, J=3 Hz: 1H); 8.66 (s: 1H).

$α_D^{20}$=−27.4°+/−0.8 in 0.5% DMSO

HPLC conditions: Chiralpak AD column, flow rate 1 cm$^3$/min,

Elution conditions from 0 to 20 min: heptane-isopropanol-ethanol-triethylamine (88/5/7/0.1 by volume)

Retention time: 15.21 min

Methyl (3RS,4RS)-4-[3-(RS)-hydroxy-3-(3-chloro-6-methoxyquinolin-4-yl)propyl]-1-H-piperidine-3-carboxylate hydrochloride 3.1 cm$^3$ of thionyl chloride, after having cooled to around −25° C. with a bath of acetone and dry ice, are added dropwise, over 45 minutes, to 5.08 g of (3RS,4RS)-4-[3(R,S)-hydroxy-(3-chloro-6-methoxyquinolin-4-yl)propyl]-1-(tert-butyloxycarbonyl)piperidine-3-carboxylic acid in 110 cm$^3$ of methanol, and the mixture is then allowed to return to 20° C. for 16 hours. The reaction mixture is then evaporated under reduced pressure (45° C.; 5 kPa). The residue is taken up with 100 cm$^3$ of isopropyl ether and triturated until a fine powder is obtained. Concentration is then carried out under reduced pressure (45° C.; 5 kPa). The product obtained is solubilized in 100 cm$^3$ of methanol. A further 3.4 cm$^3$ of thionyl chloride are added, after having cooled to around −20° C. The mixture is again allowed to stir for 16 hours and is then concentrated to dryness under reduced pressure (45° C.; 5 kPa). The residue is taken up with 60 cm³ of isopropyl ether, and concentrated to dryness under reduced pressure (45° C.; 5 kPa). 4.75 g of methyl (3RS, 4RS)-4-[3-(R,S)-hydroxy-3-(3-chloro-6-methoxyquinolin-4-yl)propyl]-1-H-piperidine-3-carboxylate in the hydrochloride form, and in the form of a beige solid, are obtained.

¹H-NMR spectrum (300 MHz, (CD₃)₂SO d6, δ in ppm): a mixture of 2 diastereoisomers in 60/40 proportions is observed. from 1.05 to 2.20 (mt: 8H); from 2.80 to 3.35 (mt: 4H); 3.46 and 3.65 (2 s: 3H in all); 3.92 and 3.93 (2 s: 3H in all); 5.48 (mt: 1H); 7.47 (dd, J=9 and 3 Hz: 1H); 7.98 (d, J=9 Hz: 1H); from 8.10 to 8.30 (unresolved peak: 1H); 8.23 (mt: 1H); 8.69 (s: 1H); from 9.00 to 9.35 (broad unresolved peak: 1H in all).

IC: m/z 393 (M+H)⁺

(3RS,4RS)-4-[3-(R,S)-hydroxy-3-(3-chloro-6-methoxyquinolin-4-yl)propyl]-1-(tert-butyloxycarbonyl)piperidine-3-carboxylic acid 100 cm³ of tert-butanol are added to 5.55 g of (3RS,4RS)-4-[3-(3-chloro-6-methoxyquinolin-4-yl)propyl]-1-(tert-butyloxycarbonyl)piperidine-3-carboxylic acid in 450 cm³ of dimethyl sulfoxide, and the reaction mixture is then saturated with oxygen for 30 minutes. A solution of 3.36 g of potassium tert-butoxide in 40 cm³ of tert-butanol is then added over 40 minutes. The mixture is allowed to stir for 2 hours while maintaining the oxygen flow rate, and then the medium is cooled to around 0° C. in order to add 1.8 cm³ of acetic acid in 30 cm³ of distilled water. 1000 cm³ of distilled water and 1000 cm³ of methyl acetate are then poured onto the reaction medium. The organic phase is then washed with 8 times 250 cm³ of distilled water then with 2 times 100 cm³ of sodium chloride. The pooled aqueous phases are re-extracted with 500 cm³ of ethyl acetate. The two organic phases are pooled and then dried over magnesium sulfate for 1 hour. Filtration is carried out through a sintered glass funnel, followed by concentration under reduced pressure (2 kPa; 45° C.). The residue is taken up in 250 cm³ of methyl acetate and 100 cm³ of distilled water. The organic phase is washed with 3 times 50 cm³ of distilled water and then with 50 cm³ of a saturated aqueous sodium chloride solution. Drying is carried out over magnesium sulfate for 1 hour, filtration is carried out through a sintered glass funnel, and then evaporation is carried out under reduced pressure (2 kPa; 45° C.). 5.08 g of (3RS,4RS)-4-[3-(R,S)-hydroxy-3-(3-chloro-6-methoxyquinolin-4-yl)propyl]-1-(tert-butyloxycarbonyl)piperidine-3-carboxylic acid are obtained.

¹H-NMR spectrum (300 MHz, (CD₃)₂SO d6, δ in ppm). A mixture of diastereoisomers is observed. * from 1.20 to 1.90 (mt: 6H); 1.38 (broad s: 9H); from 2.00 to 2.20 (mt: 1H); 2.45 (mt: 1H); from 2.65 to 4.00 (broad unresolved peak: 4H); 3.89 (s: 3H); 5.46 (mt: 1H); from 5.90 to 6.15 (broad unresolved peak: 1H); 7.43 (dd, J=9 and 3 Hz: 1H); 7.95 (d, J=9 Hz: 1H); 8.20 (mt: 1H); 8.64 and 8.65 (2s: 1H in all); from 12.70 to 12.20 (broad unresolved peak: 1H).

EI m/z=478 M⁺·
m/z=405 [M−OtBu]⁺
m/z=377 [M−BOC]⁺
m/z=223 [C₁₁H₁₀O₂NCl]⁺·
m/z=194 [223−CHO]⁺
m/z=57[C₄H₉]⁺ base peak
DCI m/z=479 MH⁺

(3RS,4RS)-4-[3-(3-chloro-6-methoxyquinolin-4-yl)propyl]-1-(tert-butyloxycarbonyl)piperidine-3-carboxylic acid 60 cm³ of a 1 N aqueous sodium hydroxide solution are added to 7.05 g of methyl (3RS,4RS)-4-[3-(3-chloro-6-methoxyquinolin-4-yl)propyl]-1-(tert-butyloxycarbonyl)piperidine-3-carboxylate in 100 cm³ of dioxane. The reaction medium is then heated at 60° C. for 2 hours and then concentrated to dryness under reduced pressure (45° C.; 5 kPa). The residue obtained is taken up with 300 cm³ of diethyl ether and 500 cm³ of distilled water. The aqueous phase is then washed with 200 cm³ of diethyl ether and then acidified with 55 cm³ of a 1 N aqueous hydrochloric acid solution. Re-extraction is then carried out with 2 times 250 cm³ of ethyl acetate. The pooled organic phases are dried over magnesium sulfate for 1 hour, then filtration is carried out through a sintered glass funnel and evaporation is carried out under reduced pressure (45° C.; 5 kPa). 5.5 g of (3RS,4RS)-4-[3-(3-chloro-6-methoxyquinolin-4-yl)propyl]-1-(tert-butyloxycarbonyl)piperidine-3-carboxylic acid, in the form of a white solid, are obtained.

¹H-NMR spectrum (400 MHz, (CD₃)₂SO d6, δ in ppm): from 1.35 to 1.95 (mt: 7H); 1.39 (s: 9H); from 2.45 to 2.60 (mt: 1H); from 2.85 to 4.00 (broad unresolved peak: 4H); 3.20 (broad t, J=6 Hz: 2H); 3.97 (broad s: 3H); 7.38 (d, J=3 Hz: 1H); 7.45 (dd, J=9 and 3 Hz: 1H); 7.96 (d, J=9 Hz: 1H); 8.67 (s: 1H); from 11.90 to 12.50 (mf very broad unresolved peak: 1H).

IC: m/z 463 (M+H)⁺

Methyl (3RS,4RS)-4-[3-(3-chloro-6-methoxyquinolin-4-yl)propyl]-1-(tert-butyloxycarbonyl)piperidine-3-carboxylate 5.85 g of methyl (3RS,4RS)-1-(tert-butyloxycarbonyl)-4-allylpiperidine-3-carboxylate (isomer A), solubilized in 60 cm³ of tetrahydrofuran, are added to 72 cm³ of a 0.5 M solution of 9-borabicyclo[3,3,1]-nonane in tetrahydrofuran with stirring and under an inert atmosphere, and after having cooled to 0° C. The mixture is then returned to a temperature in the region of 20° C., while the stirring is continued for a further 4 hours. 6.03 g of 4-bromo-3-chloro-t-methoxyquinoline in solution of 200 cm³ of tetrahydrofuran are added over 45 minutes, followed by 440 mg of palladiumdiphenylphosphinoferrocene chloride and, finally, 12.8 g of tripotassium phosphate. The reaction mixture is heated for 15 hours at reflux and then filtered through a sintered glass funnel under hot conditions. The filtrate is taken up in 4 times 20 cm³ of ethyl acetate and concentrated to dryness under reduced pressure (45° C.; 5 kPa). The residue is taken up with 250 cm³ of ethyl acetate and 200 cm³ of water. The organic phase is separated after settling out, washed with 3 times 50 cm³ of distilled water and with 2 times 100 cm³ of a saturated aqueous sodium chloride solution, dried over magnesium sulfate, filtered, and then concentrated under reduced pressure (45° C.; 5 kPa). The residue is purified by chromatography, under an argon pressure of 150 kPa, on a column of silica gel (particle size 20/45 μ; diameter 8 cm; height 35 cm), eluting with a mixture of cyclohexane-ethyl acetate (73/27 by volume) and collecting fractions of 200 cm³. Fractions 8 to 16 are pooled, and then concentrated under reduced pressure (45° C.; 5 kPa). 9.5 g of methyl (3RS,4RS)-4-[3-(3-chloro-6-methoxyquinolin-4-yl)4-propyl[-1-[tert-butyloxycarbonyl)piperidine-3-carboxylate, in the form of a colorless oil, are obtained.

¹H-NMR spectrum (300 MHz (CD₃)₂SO d6, δ in ppm): from 1.30 to 1.90 (mt: 7H); 1.37 (s: 9H); 2.63 (mt: 1H); from 2.70 to 3.25 (unresolved peak: 2H); 3.18 (broad t, J=7.5 Hz: 2H); 3.51 (broad s: 3H); from 3.60 to 4.00 (unresolved peak: 2H); 3.97 (s: 3H); 7.38 (d, J=3 Hz: 1H); 7.45 (dd, J=9 and 3 Hz: 1H); 7.96 (d, J=9 Hz: 1H); 8.67 (s: 1H).

EI: m/z 476 (M⁺·), m/z 375, 207, 194, 170, 58 (base peak)

The 4-bromo-3-chloro-6-methoxyquinoline is described in patent application WO 20024074.

Syntheses of the 2 pairs of stereoisomers of methyl 1-(tert-butyloxycarbonyl)-4-allylpiperidine-3-carboxylate Methyl (3RS,4RS)-1-(tert-butyloxycarbonyl)-4-allylpiperidine-3-carboxylate (isomer A, racemic)
Methyl (3RS,4RS)-1-(tert-butyloxycarbonyl)-4-allylpiperidine-3-carboxylate (isomer B, racemic)

A solution of 32.43 g of methyl 1-(tert-butyloxycarbonyl)-4-allyl-4-(methoxyoxalyloxy)hydroxypiperidine-3-carboxylate (racemic A) in 600 cm³ of toluene under an inert atmosphere is heated to a temperature of 110° C. 200 mg of AIBN are then rapidly added, followed by 35.06 cm³ of tributyltin hydride and then a further 200 mg of AIBN. The medium is maintained at 110° C. for 4 hours. The mixture is then cooled to a temperature close to 20° C. for 12 hours, and 300 cm³ of distilled water are then added. The organic phase is rewashed with 3 times 300 cm³ of distilled water and then dried over magnesium sulfate, filtered through a sintered glass funnel, and concentrated to dryness under reduced pressure (45° C.; 5 kPa). The residue is purified by chromatography, under a nitrogen pressure of 50 kPa, on a column of silica gel (particle size 0.06–0.2 mm; diameter 12 cm; height 75 cm), eluting with a mixture of cyclohexane-ethyl acetate (80/20 by volume) and collecting fractions of 100 cm³. Fractions 45 to 103 are pooled and then concentrated. 16.05 g of a mixture of isomers (A+B) of methyl 1-(tert-butyloxycarbonyl)-4-allylpiperidine-3-carboxylate, in the form of a light yellow oil, are obtained.

$^1$H-NMR spectrum (300 Mhz, (CD$_3$)$_2$SO d6, δ in ppm): 1.38 (s: 9H); 1.43 (mt: 1H); 1.75 (mt: 1H); 1.66 (mt: 1H); 2.06 (mt: 2H); 2.61 (q, J=5.5 Hz: 1H); from 2.75 to 3.15 (broad unresolved peak: 1H); 3.20 (dd, J=13.5 and 5.5 Hz: 1H); 3.59 (broad s: 3H); from 3.60 to 4.10 (broad unresolved peak: 2H); 5.01 (mt: 2H); 5.75 (mt: 1H)

IC: m/z 284 (M+H)$^+$

Using the mixture of isomers (A+B) obtained above, the separation of the 2 pairs of isomers is carried out by HPLC.

The separation of A (racemic) and B (racemic) is carried out on a Kromasil C8 stationary phase using 16.08 g of the mixture A+B described above (particle size 10 μmm; diameter 80 mm; mass of the stationary phase 1.25 kg), under a pressure of 600 kPa, the mobile phase is composed of a mixture of acetone-distilled water (60/40 by volume) having a flow rate of 126 cm³ per minute, and the wavelength of the UV detector is set at 215 nm. The fractions containing the first isomer noted A (racemic) are pooled and evaporated under reduced pressure (2 kPa) at a temperature in the region of 40° C. 6.55 g of methyl (3RS,4RS)-1-(tert-butyloxycarbonyl)-4-allylpiperidine-3-carboxylate are obtained. The fractions containing the second isomer noted B (racemic) are pooled and evaporated under reduced pressure (2 kPa) at a temperature in the region of 40° C. 2.35 g of methyl (3RS,4RS)-1-(tert-butyloxycarbonyl)-4-allylpiperidine-3-carboxylate are obtained.

Isomer A (Racemic)

$^1$H-NMR spectrum (300 MHz, (CD$_3$)$_2$SO d6, δ in ppm): 1.38 (s: 9H); 1.43 (mt: 1H); 1.75 (mt: 1H); 1.66 (mt: 1H); 2.06 (mt: 2H); 2.61 (q, J=5.5 Hz: 1H); from 2.75 to 3.15 (broad unresolved peak: 1H); 3.20 (dd, J=13.5 and 5.5 Hz: 1H); 3.59 (broad s: 3H); from 3.60 to 4.10 (broad unresolved peak: 2H); 5.01 (mt: 2H); 5.75 (mt: 1H).

IC: m/z 284 (M+H)$^+$

HPLC Conditions: preparative column, Kromasil C8, flow rate 1 cm³/min, elution conditions from 0 to 16 min: acetonitrile-distilled water (60/40)

Retention time: 13.18 min

Isomer B (Racemic)

$^1$H-NMR spectrum (400 MHz, (CD$_3$)$_2$SO d6, δ in ppm): at a temperature of 373K: 1.13 (mt: 1H); 1.43 (s: 9H); 1.73 (dq, J=14 and 4 Hz: 1H); 1.87 (mt: 1H); 1.97 (mt: 1H); 2.15 (mt: 1H); 2.21 (double t, J=10 and 4 Hz: 1H); 2.83 (ddd, J=13.5–12 and 3 Hz: 1H); 2.89 (dd, J=13 and 11 Hz: 1H); 3.67 (s: 3H); 3.89 (d mt, J=13.5 Hz: 1H); 4.02 (ddd, J=13–4 and 2 Hz: 1H); 5.04 (mt: 2H); 5.76 (mt: 1H).

IC: m/z 284 (M+H)$^+$

HPLC conditions: preparative column, Kromasil C8, flow rate 1 cm³/min, elution condition from 0 to 16 min: acetonitrile-distilled water (60/40)

Retention time: 11.37 min

Methyl 1-(tert-butyloxycarbonyl)-4-allyl-4-(methoxyoxalyloxy)-hydroxypiperidine-3-carboxylate Under an inert atmosphere, 45.5 g of dimethylaminopyridine are added to a solution of 36.8 g of methyl 1-(tert-butyloxycarbonyl)-4-allyl-4-hydroxypiperidine-3-carboxylate in 400 cm³ of acetonitrile and then 35.32 cm³ of oxalyl chloride are added over 30 minutes. After stirring for 20 minutes at a temperature close to 20° C., the reaction mixture is taken up with 300 cm³ of ethyl acetate and 500 cm³ of a saturated aqueous sodium bicarbonate solution. The organic phase is separated after settling out, and washed with 6 times 300 cm³ of distilled water then with 2 times 300 cm³ of a saturated aqueous sodium chloride solution. Similarly, the aqueous phase is washed with 3 times 300 cm³ of methyl acetate. The pooled organic phases are dried over magnesium sulfate and filtered through a sintered glass funnel. The residue is purified by chromatography, under a nitrogen pressure of 50 kPa, on a column of silica gel (particle size 40–60 μm; diameter 8 cm; height 60 cm), eluting with a mixture of cyclohexane-ethyl acetate (70/30 by volume) and collecting fractions of 250 cm³. Fractions 19 to 37 are pooled and then concentrated under reduced pressure. 23.31 g of a mixture of isomers (A+B) of methyl 1-(tert-butyloxycarbonyl)-4-allyl-4-(methoxyoxalyloxy)hydroxypiperidine-3-carboxylate, in the form of a pale yellow oil, are obtained.

$^1$H-NMR spectrum (300 MHz, (CD$_3$)$_2$SO d6, δ in ppm). A mixture of diastereoisomers in 65/35 proportions is observed. * 1.39 and 1.42 (2 s: 9H in all); 1.85–2.17 and 2.32 (3 mts: 2H in all); 2.65 (dd, J=15 and 7.5 Hz: 0.35 H); from 2.75 to 2.95 (mt: 1H); 3.01 (mt: 0.65H); 3.05 (dd, J=15 and 7.5 Hz: 0.65 H); 3.17 (mt: 0.35 H); from 3.25 to 3.75 (unresolved peak: 4H); 3.61 (broad s: 3H); 3.81 and 3.82 (2 s: 3H in all); from 5.00 to 5.25 (mt: 2H); 5.78 (mt: 1H).

Using the mixture of isomers A+B obtained above, the separation of the two pairs of isomers is carried out by HPLC on a Kromasil C8 stationary phase using 196.59 g of the mixture A+B described above (preparative column; particle size 10 μmm; diameter 80 mm; mass of the stationary phase 1.2 kg), under a pressure of 600 kPa, the mobile phase is composed of a mixture of acetone-distilled water-methanol (60/30/10 by volume) having a flow rate of 126 cm³ per minute, and the wavelength of the UV detector is set at 215 nm. The fractions containing the first isomer A (racemic) are pooled and evaporated under reduced pressure (2 kPa) at a temperature in the region of 40° C. 32.43 g of isomer A in the form of an oil are obtained. The fractions containing the second isomer noted B (racemic) are pooled and evaporated under reduced pressure (2 kPa) at a temperature in the range of about 40° C. 35.25 g of isomer B in the form of an oil are obtained.

Isomer A (Racemic)

$^1$H-NMR spectrum (300 MHz, (CD$_3$)$_2$SO d6, δ in ppm): 1.41 (s: 9H); 1.86 (mt: 1H); 2.33 (mt: 1H); 2.87 (broad dd, J=14.5 and 7.5 Hz: 1H); from 2.95 to 3.10 (mt: 2H); from 3.25 to 3.75 (broad unresolved peak: 4H); 3.62 (broad s: 3H); 3.81 (s: 3H); from 5.10 to 5.25 (mt: 2H); 5.80 (mt: 1H).

IC: m/z 386 (M+H)$^+$, m/z 403 (M+NH$_4$)$^+$

HPLC conditions: preparative column, Kromasil C8, flow rate 1 cm$^3$/min, elution conditions from 0 to 10 min: acetonitrile-distilled water (60/40)

Retention time: 7.39 min

Isomer B (Racemic)

$^1$H-NMR spectrum (300 MHz, (CD$_3$)$_2$SO d6, δ in ppm); 1.39 (s: 9H); 2.18 (mt: 2H); 2.66 (dd, J=15 and 7.5 Hz: 1H); 2.83 (dd, J=15 and 7 Hz: 1H); from 2.85 to 3.10 (mt: 1H); 3.18 (mt: 1H); from 3.30 to 3.55 (unresolved peak: 1H); 3.66 (very broad s: 3H); from 3.75 to 3.95 (unresolved peak: 1H); 3.83 (s: 3H); 4.00 (very broad d, J=13.5 Hz: 1H); 5.07 (dd, J=18 and 1.5 Hz: 1H); 5.15 (dd, J=10.5 and 1.5 Hz: 1H); 5.75 (mt: 1H).

IC: m/z 386 (M+H)$^+$ (base peak), m/z 403 (M+NH$_4$)$^+$

HPLC conditions: preparative column, Kromasil C8, flow rate 1 cm$^3$/min, elution conditions from 0 to 10 min: acetonitrile-distilled water (60/40)

Retention time: 7.98 min

EXAMPLE 2

Synthesis of the 4 Stereoisomers of (3RS,4RS)-4-[3-(R,S)-hydroxy-3-(3-chloro-6-methoxyquinolin-4-yl)propyl]-1-[2-(2-thienylsulfanyl)ethyl]piperidine-3-carboxylic acid (3R,4R)-4-[(3R)-hydroxy-3-(3-chloro-6-methoxyquinolin-4-yl)propyl]-1-[2-(2-thienylsulfanyl)ethyl]piperidine-3-carboxylic acid (3R,4R)-4-[(3S)-hydroxy-3-(3-chloro-6-methoxyquinolin-4-yl)propyl]-1-[2-(2-thienylsulfanyl)ethyl]piperidine-3-carboxylic acid (3S,4S)-4-[(3R)-hydroxy-3-(3-chloro-6-methoxyquinolin-4-yl)propyl]-1-[2-(2-thienylsulfanyl)ethyl]piperidine-3-carboxylic acid (3S,4S)-4-[(3S)-hydroxy-3-(3-chloro-6-methoxyquinolin-4-yl)propyl]-1-[2-(2-thienylsulfanyl)ethyl]piperidine-3-carboxylic acid The four stereoisomers are hereinafter referred to as A, B, C, and D. Their absolute stereochemistries are not known.

Stereoisomer A 2.7 cm$^3$ of a 1 N aqueous sodium hydroxide solution are added to 480 mg of methyl 4-[3-hydroxy-3-(3-chloro-6-methoxyquinolin-4-yl)propyl]-1-[2-(2-thienylsulfanyl)ethyl]piperidine-3-carboxylate (ester isomer A) solubilized in 10 cm$^3$ of dioxane. The reaction medium is then heated at 70° C. for 5 h 30 min. The temperature is then allowed to return to 19° C. for 12 hours. Evaporation is carried out under reduced pressure (20 kPa; 45° C.). The residue is taken up in 25 cm$^3$ of distilled water and then extraction is carried out with 25 cm$^3$ of diethyl ether. The aqueous phase is acidified with 2.6 cm$^3$ of a 1 N aqueous hydrochloric acid solution (pH=6) and then this phase is extracted with 3 times 70 cm$^3$ of ethyl acetate. The organic phase is dried under magnesium sulfate, filtered through a sintered glass funnel, and then evaporated under reduced pressure (20 kPa; 45° C.). After having dried under vacuum (50 kPa) for 4 hours, 360 mg of 4-[3-hydroxy-3-(3-chloro-6-methoxyquinolin-4-yl)propyl]-1-[2-(2-thienylsulfanyl)ethyl]piperidine-3-carboxylic acid, in the form of a pale yellow solid (isomer A), are obtained.

$^1$H-NMR spectrum (300 MHz, (CD$_3$)$_2$SO d6, δ in ppm): 1.34 (mt: 1H); from 1.45 to 1.90 (mt: 5H); from 2.00 to 2.15 (mt: 1H); from 2.15 to 2.35 (mt: 1H); 2.40 (very broad d, J=10.5 Hz: 1H); from 2.45 to 2.60 (mt: 1H); 2.58 (t, J=7.5 Hz: 2H) from 2.60 to 2.95 (unresolved peak: 2H); 2.96 (mt: 2H); 3.89 (s: 3H); 5.47 (mt: 1H); 6.09 (mf: 1H); 7.07 (dd, J=5.5 and 3.5 Hz: 1H); 7.21 (dd, J=3.5 and 1 Hz: 1H); 7.44 (dd, J=9 and 3 Hz: 1H); 7.64 (dd, J=5.5 and 1 Hz: 1H); 7.96 (d, J=9 Hz: 1H); 8.20 (d, J=3 Hz: 1H); 8.65 (s: 1H).

α$_D$$^{20}$=28.2°+/−0.9 in 0.5% methanol

Stereoisomer B 2.7 cm$^3$ of a 1 N aqueous sodium hydroxide solution are added to 478 mg of methyl 4-[3-hydroxy-3-(3-chloro-6-methoxyquinolin-4-yl)propyl]-1-[2-(2-thienylsulfanyl)ethyl]piperidine-3-carboxylate (ester isomer B) solubilized in 10 cm$^3$ of dioxane. The reaction medium is then heated at 70° C. for 5 h 30 min. The temperature is then allowed to return to 19° C. for 12 hours. Evaporation is carried out under reduced pressure (20 kPa; 45° C.). The residue is taken up in 25 cm$^3$ of distilled water and then extraction is carried out with 25 cm$^3$ of diethyl ether. The aqueous phase is acidified with 2.6 cm$^3$ of a 1 N aqueous hydrochloric acid solution (pH=6) and then this phase is extracted with 3 times 70 cm$^3$ of ethyl acetate. The organic phase is dried under magnesium sulfate, filtered through a sintered glass funnel, and then evaporated under reduced pressure (20 kPa; 45° C.). After having dried under vacuum (50 kPa) the residue is taken up with 25 cm$^3$ of acetone and then concentrated again under reduced pressure (20 kPa; 45° C.). Drying is carried out under reduced pressure (50 kPa; 20° C.) for 4 hours and 350 mg of 4-[3-hydroxy-3-(3-chloro-6-methoxyquinolin-4-yl)propyl]-1-[2-(2-thienylsulfanyl)ethyl]piperidine-3-carboxylic acid, in the form of a pale yellow solid (isomer B), are obtained.

$^1$H-NMR spectrum (300 MHz, (CD$_3$)$_2$SO d6, δ in ppm): 1.32 (mt: 1H); from 1.45 to 1.90 (mt: 5H); from 2.00 to 2.15 (mt: 1H); from 2.15 to 2.35 (mt: 1H); 2.37 (very broad d, J=10.5 Hz: 1H); from 2.45 to 2.60 (mt: 1H); 2.59 (t, J=7.5 Hz: 2H); from 2.65 to 3.00 (mt: 2H); 2.96 (mt: 2H); 3.90 (s: 3H); 5.46 (mt: 1H); 6.05 (unresolved peak: 1H); 7.07 (dd, J=5.5 and 3.5 Hz: 1H); 7.21 (dd, J=3.5 and 1 Hz: 1H); 7.43 (dd, J=9 and 3 Hz: 1H); 7.64 (dd, J=5.5 and 1 Hz: 1H); 7.95 (d, J=9 Hz: 1H); 8.20 (d, J=3 Hz: 1H); 8.65 (s: 1H); from 12.80 to 13.40 (broad unresolved peak: 1H).

α$_D$$^{20}$=−25.2°+/−1.5 in 0.5% methanol

Stereoisomer C 1.7 cm$^3$ of a 1 N aqueous sodium hydroxide solution are added to 300 mg of methyl 4-[3-hydroxy-3-(3-chloro-6-methoxyquinolin-4-yl)propyl]-1-[2-(2-thienylsulfanyl)ethyl]piperidine-3-carboxylate (ester isomer C) solubilized in 10 cm$^3$ of dioxane. The reaction medium is then heated at 70° C. for 5 h 30 min. The temperature is allowed to return to 19° C. for 12 hours and then heating is carried out again at 70° C. for 2 hours. Evaporation is then carried out under reduced pressure (20 kPa; 45° C.). The residue is taken up in 25 cm$^3$ of distilled water and then extraction is carried out with 25 cm$^3$ of diethyl ether. The aqueous phase is acidified with 1.6 cm$^3$ of a 1 N aqueous hydrochloric acid solution (pH=6) and then this phase is extracted with 3 times 70 cm$^3$ of ethyl acetate. The organic phase is dried under magnesium sulfate, filtered through a sintered glass funnel, and then evaporated under reduced pressure (20 kPa; 45° C.). After having dried under vacuum (50 kPa), the residue is taken up with 20 cm$^3$ of acetone and then concentrated again under reduced pressure (20 kPa; 45° C.). Drying is carried out under reduced pressure (50 kPa; 20° C.) for 12 hours and 250 mg of 4-[3-hydroxy-3-(3-chloro-6-methoxyquinolin-4-yl)propyl]-1-[2-(2-thienylsulfanyl)ethyl]piperidine-3-carboxylic acid, in the form of a pale yellow solid (isomer C), are obtained.

¹H-NMR spectrum (300 MHz, (CD₃)₂SO d6, δ in ppm): 1.30 (mt: 1H); from 1.45 to 1.85 (mt: 5H); 2.19 (mt: 2H); 2.37 (very broad d, J=11 Hz: 1H); from 2.45 to 2.80 (mt: 2H); 2.58 (t, J=7.5 Hz: 2H); from 2.80 to 3.10 (unresolved peak: 1H); 2.96 (mt: 2H); 3.91 (s: 3H); 5.45 (mt: 1H); 6.11 (broad unresolved peak: 1H); 7.07 (dd, J=5.5 and 3.5 Hz: 1H); 7.22 (dd, J=3.5 and 1 Hz: 1H); 7.43 (dd, J=9 and 3 Hz: 1H); 7.65 (dd, J=5.5 and 1 Hz: 1H); 7.95 (d, J=9 Hz: 1H); 8.24 (d, J=3 Hz: 1H); 8.65 (s: 1H).

$\alpha_D^{20}$=88.1°+/−1.5 in 0.5% methanol

Stereoisomer D 1.8 cm³ of a 1 N aqueous sodium hydroxide solution are added to 325 mg of methyl 4-[3-hydroxy-3-(3-chloro-6-methoxyquinolin-4-yl)propyl]-1-[2-(2-thienylsulfanyl)ethyl]piperidine-3-carboxylate (ester isomer D) solubilized in 10 cm³ of dioxane. The reaction medium is then heated at 70° C. for 5 h 30 min. The temperature is allowed to return to 19° C. for 12 hours and then heating is carried out again at 70° C. for 2 hours. Evaporation is then carried out under reduced pressure (20 kPa; 45° C.). The residue is taken up in 25 cm³ of distilled water and then extraction is carried out with 25 cm³ of diethyl ether. The aqueous phase is acidified with 1.6 cm³ of a 1 N aqueous hydrochloric acid solution (pH=6) and then this phase is extracted with 3 times 70 cm³ of ethyl acetate. The organic phase is dried under magnesium sulfate, filtered through a sintered glass funnel, and then evaporated under reduced pressure (20 kPa; 45° C.). After having dried under vacuum (50 kPa), the residue is taken up with 20 cm³ of acetone and then concentrated again under reduced pressure (20 kPa; 45° C.). Drying is carried out under reduced pressure (50 kPa; 20° C.) for 12 hours and 260 mg of 4-[3-hydroxy-3-(3-chloro-6-methoxyquinolin-4-yl)propyl]-1-[2-(2-thienylsulfanyl)ethyl]piperidine-3-carboxylic acid, in the form of a pale yellow solid (isomer D), are obtained.

¹H-NMR spectrum (300 MHz, (CD₃)₂SO d6, δ in ppm): 1.30 (mt: 1H); from 1.40 to 1.85 (mt: 5H); 2.19 (mt: 2H); 2.37 (very broad d, J=10.5 Hz: 1H); 2.58 (t, J=7.5 Hz: 2H); from 2.60 to 2.75 (mt: 1H); from 2.80 to 3.05 (mt: 1H); 2.96 (mt: 2H); 3.90 (s: 3H); 5.45 (mt: 1H); 6.09 (mt: 1H); 7.07 (dd, J=5,5 and 3.5 Hz: 1H); 7.22 (dd, J=3.5 and 1 Hz: 1H ; 7.43 (dd, J=9 and 3 Hz: 1H); 7.64 (dd, J=5.5 and 1 Hz: 1H); 7.95 (d, J=9 Hz: 1H); 8.23 (d, J=3 Hz: 1H); 8.65 (s: 1H).

$\alpha_D^{20}$=−88.1°+/−1.5 in 0.5% methanol

Synthesis of the 4 Stereoisomers of Methyl (3RS,4RS)-4-[3-(R,S)-hydroxy-3-(3-chloro-6-methoxyquinolin-4-yl) propyl]-1-[2-(2-thienylsulfanyl)ethyl]piperidine-3-carboxylate Methyl (3R,4R)-4-[(3R)-hydroxy-3-(3-chloro-6-methoxyquinolin-4-yl)propyl]-1-[2-(2-thienylsulfanyl) ethyl]piperidine-3-carboxylate Methyl (3R,4R)-4-[(3S)-hydroxy-3-(3-chloro-6-methoxyquinolin-4-yl)propyl]-1-[2-(2-thienylsulfanyl) ethyl]piperidine-3-carboxylate Methyl (3S,4S)-4-[(3R)-hydroxy-3-(3-chloro-6-methoxyquinolin-4-yl)propyl]-1-[2-(2-thienylsulfanyl) ethyl]piperidine-3-carboxylate Methyl (3S,4S)-4-[(3S)-hydroxy-3-(3-chloro-6-methoxyquinolin-4-yl)propyl]-1-[2-(2-thienylsulfanyl) ethyl]piperidine-3-carboxylate The four stereoisomers are hereinafter referred to as A, B, C, and D. Their absolute stereochemistries are not known.

1.5 cm³ of triethylamine, 2.15 g of potassium carbonate and 0.85 g of potassium iodide are added to 2.5 g of methyl (3RS,4RS)-4-[3-(R,S)-hydroxy-3-(3-chloro-6-methoxyquinolin-4-yl)propyl]-1-H-piperidine-3-carboxylate hydrochloride solubilizes in 110 cm³ of acetonitrile. Still at 20° C., 1.15 g of 2-(bromoethylsulfanyl) thiophene are added. The reaction medium is then brought to 60° C. for 16 hours. Next, the medium is allowed to return to 20° C. and is then evaporated under reduced pressure (45° C.; 5 kPa). The residue is taken up with 200 cm³ of ethyl acetate and 100 cm³ of distilled water. The organic phase is rewashed two times with 100 cm³ of a saturated aqueous sodium chloride solution, dried over magnesium sulfate for 1 hour, filtered through a sintered glass funnel, and then evaporated under reduced pressure (45° C.; 5 kPa). The residue is purified by chromatography, under a nitrogen pressure of 50 kPa, on a column of silica gel (particle size 0.065–0.2 μ; diameter 2.5 cm; height 35 cm), eluting with a mixture of cyclohexane-ethyl acetate (60/40 by volume) and collecting fractions of 50 cm³. Fractions 6 to 9 are pooled, and then concentrated under reduced pressure (45° C.; 5 kPa). 1.95 g of methyl (3RS,4RS)-4-[3-(R,S)-hydroxy-3-(3-chloro-6-methoxyquinolin-4-yl)propyl]-1-[2-(2-thienylsulfanyl)ethyl]piperidine-3-carboxylate (mixture of isomers A, B, C and D), in the form of a colorless oil, are obtained.

The 2-(bromoethylsulfanyl)thiophene may be prepared according to patent WO 200125227.

¹H-NMR spectrum (300 MHz, (CD₃)₂SO d6, δ in ppm). A mixture of 2 diastereoisomers in 60/40 proportions is observed. * from 1.10 to 1.85 (mt: 7H); from 1.85 to 2.85 (mt: 7H); 2.89 (broad t, J=7.5 Hz: 2H); 3.42 and 3.56 (2 s: 3H in all); 3.89 and 3.90 (2 s: 3H in all); 5.45 (mt: 1H); 6.01 (broad s: 1H); 7.05 (dd, J=5.5 and 3.5 Hz: 1H); 7.18 (dd, J=3.5 and 1.5 Hz: 1H); 7.44 (dd, J=9 and 3 Hz: 1H); 7.61 (dd, J=5.5 and 1.5 Hz: 1H); 7.95 (d, J=9 Hz: 1H); 8.19 (mt: 1H); 8.65 and 8.66 (2 s: 1H in all).

EI: m/z 534 (M⁺·), m/z 504 (base peak)

Using the mixture of stereoisomers A, B, C, D obtained above, the separation of each stereoisomer is carried out by HPLC.

The separation of the 2 pairs of stereoisomers (A+B) and (C+D) is carried out on a C18 Symmetry stationary phase using 1.95 g of the mixture A, B, C, and D described above (particle size 7 μmm; diameter 60 mm; mass of the stationary phase 700 g), under a pressure of 500 kPa, the mobile phase is composed of a mixture of methanol-aqueous buffer solution (pH 4.9-acetonitrile (10/55/35 by volume) having a flow rate of 120 cm³ per minute, and the wavelength of the UV detector is set at 280 nm. The fractions containing the first pair of enantiomers noted (A+B) are pooled and evaporated under reduced pressure (2 kPa) at a temperature in the region of 40° C. The residue obtained is taken up with water and then extracted twice with dichloromethane. The organic phase is dried over magnesium sulfate, filtered, and then evaporated under reduced pressure (2 kPa; 45° C.). 640 mg of methyl 4-[3-hydroxy-3-(3-chloro-6-methoxyquinolin-4-yl)propyl]-1-[2-(2-thienylsulfanyl)ethyl]piperidine-3-carboxylate (mixture A+B) are obtained.

The fractions containing the second pair of enantiomers noted (C+D) are pooled and evaporated under reduced pressure (2 kPa) at a temperature in the region of 40° C. The residue obtained is taken up in water and then extracted twice with dichloromethane. The organic phase is dried over magnesium sulfate, filtered, and then evaporated under reduced pressure (2 kPa; 45° C.). 620 mg of methyl 4-[3-hydroxy-3-(3-chloro-6-methoxyquinolin-4-yl)propyl]-1-[2-(2-thienylsulfanyl)ethyl]piperidine-3-carboxylate (mixture C+D) are obtained.

Next, the products of the pair of enantiomers (A, B) are separated on a chiracel OJ column (particle size 20 μmm;

diameter 35 mm; mass of the stationary phase 700 g) under a pressure of 1510 kPa, the mobile phase is composed of a mixture of heptane-ethanol-triethylamine (90/10/0.1 by volume) having a flow rate of 120 cm³ per minute, and the wavelength of the UV detector is set at 254 nm. The fractions containing each product are isolated and then concentrated under reduced pressure (2 kPa) at a temperature in the region of 45° C.; 0.48 g of the stereoisomer A and 0.478 g of the stereoisomer B are obtained.

Similarly, the products of the pair of enantiomers (C, D) are separated on a chiracel OD column (particle size 20 μmm; diameter 80 mm; mass of the stationary phase 1250 g) under a pressure of 1510 kPa, the mobile phase is composed of a mixture of heptane-isopropanol-methanol-triethylamine (90/4/3/0.1 by volume) having a flow rate of 150 cm³ per minute, and the wavelength of the UV detector is set at 265 nm. The fractions containing each product are isolated and then concentrated under reduced pressure (2 kPa) at a temperature in the region of 40° C.; 0.30 g of the stereoisomer C, in the form of a whitish solid, and 0.325 g of the stereoisomer D in the form of a whitish solid, are obtained.

Stereoisomer A $^1$H-NMR spectrum (400 MHz, (CD$_3$)$_2$SO d6, δ in ppm): 1.30 (mt: 1H); 1.53 (mt: 1H); from 1.65 to 1.85 (mt: 4H); 2.10 (mt: 1H); 2.22 (mt: 1H); 2.39 (dd, J=12 and 4 Hz: 1H); from 2.45 to 2.60 (mt: 3H); 2.64 (mt: 1H); 2.73 (dd, J=12 and 6.5 Hz: 1H); 2.91 (t, J=7 Hz: 2H); 3.45 (s: 3H); 3.92 (s: 3H); 5.49 (mt: 1H); 5.79 (unresolved peak: 1H); 7.04 (dd, J=5.5 and 3.5 Hz: 1H); 7.16 (dd, J=3.5 and 1 Hz: 1H); 7.43 (dd, J=9 and 3 Hz: 1H); 7.56 (dd, J=5.5 and 1 Hz: 1H); 7.96 (d, J=9 Hz: 1H); 8.21 (d, J=3 Hz: 1H); 8.63 (s: 1H).

$\alpha_D^{20}$=−28.8°+/−0.7 in 0.5% of dichloromethane

HPLC conditions: Chiralcel OJ column, flow rate 1 cm³/min,

Elution conditions from 0 to 35 min; ethanol-heptane-triethylamine (10/90/0.1 by volume)

Retention time: 18.54 min

Stereoisomer B $^1$H-NMR spectrum (300 MHz, (CD$_3$)$_2$SO d6, δ in ppm): from 1.05 to 1.35 (mt: 1H); 1.51 (mt: 1H); 1.72 (mt: 4H); from 2.00 to 2.25 (mt: 2H); 2.32 (broad d, J=11 Hz: 1H); from 2.40 to 2.55 (mt: 3H); 2.64 (mt: 1H); 2.73 (mt: 1H); 2.89 (t, J=7.5 Hz: 2H); 3.41 (s: 3H); 3.88 (s: 3H); 5.45 (mt: 1H); 6.03 (d, J=3.5 Hz: 1H); 7.05 (dd, J=5.5 and 3.5 Hz: 1H); 7.18 (dd, J=3.5 and 1 Hz: 1H); 7.44 (dd, J=9 and 3 Hz: 1H); 7.62 (dd, J=5.5 and 1 Hz: 1H); 7.96 (d, J=9 Hz: 1H); 8.19 (d, J=3 Hz: 1H); 8.65 (s: 1H).

$\alpha_D^{20}$=−31.7°+/−0.8 in 0.5% dichloromethane

HPLC conditions: Chiralcel OJ column, flow rate 1 cm³/min,

Elution conditions from 0 to 35 min: ethanol-heptane-triethylamine (10/90/0.1 by volume)

Retention time: 24.31 min

Stereoisomer C $^1$H-NMR spectrum (300 MHz, (CD$_3$)$_2$SO d6, δ in ppm): 1.43 (mt: 2H); from 1.55 to 1.85 (mt: 4H); 1.96 (mt: 1H); 2.13 (mt: 1H); 2.32 (very broad d, J=11 Hz: 1H); from 2.35 to 2.60 (mt: 3H); 2.67 (mt: 1H); 2.76 (mt: 1H); 2.88 (t, J=7.5 Hz: 2H); 3.56 (s: 3H); 3.89 (s: 3H); 5.45 (mt: 1H); 6.02 (d, J=3.5 Hz: 1H); 7.05 (dd, J=5.5 and 3.5 Hz: 1H); 7.17 (dd, J=3.5 and 1 Hz: 1H); 7.44 (dd, J=9 and 3 Hz: 1H); 7.61 (dd, J=5.5 and 1 Hz: 1H); 7.95 (d, J=9 Hz: 1H); 8.19 (d, J=3 Hz: 1H); 8.66 (s: 1H).

$\alpha_D^{20}$=27.8°+/−0.8 in 0.5% DMSO

HPLC conditions: Chiralcel OD column, flow rate 1 cm³/mim,

Elution conditions from 0 to 35 min: heptane-isopropanol-ethanol-triethylamine (93/4/3/0.1 by volume)

Retention time: 16.19 min

Stereoisomer D $^1$H-NMR spectrum (300 MHz, (CD$_3$)$_2$SO d6, δ in ppm): 1.44 (mt: 2H); from 1.55 to 1.85 (mt: 4H); 1.97 (mt: 1H); 2.14 (mt: 1H); 2.32 (very broad d, J=11 Hz: 1H); from 2.35 to 2.60 (mt: 3H); 2.67 (mt: 1H); 2.76 (mt: 1H); 2.88 (t, J=7.5 Hz: 2H); 3.56 (s: 3H); 3.89 (s: 3H); 5.44 (mt: 1H); 6.03 (d, J=4 Hz: 1H); 7.06 (dd, J=5.5 and 3.5 Hz: 1H); 7.18 (dd, J=3.5 and 1 Hz: 1H); 7.44 (dd, J=9 and 3 Hz: 1H); 7.62 (dd, J=5.5 and 1 Hz: 1H); 7.95 (d, J=9 Hz: 1H); 8.20 (d, J=3 Hz: 1H); 8.66 (s: 1H).

$\alpha_D^{20}$=−30.0°+/−0.8 in 0.5% DMSO

HPLC conditions: Chiralcel OD column, flow rate 1 cm³/min,

Elution conditions from 0 to 35 min: heptane-isopropanol-ethanol-triethylamine (93/4/3/0.1 by volume)

Retention time: 19.41 min

What is claimed is:

1. A compound of the formula (I):

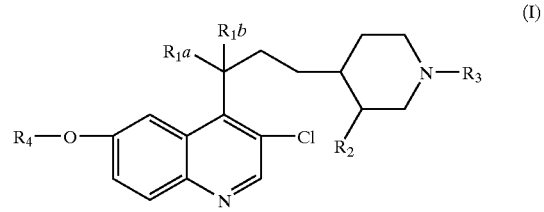

wherein:

R$_{1a}$ is hydrogen, halogen, hydroxyl, amino, alkylamino, dialkylamino, hydroxyamino, alkoxyamino or alkylalkoxyamino; and R$_{1b}$ is hydrogen; or R$_{1a}$ and R$_{1b}$ form an oxo group;

R$_2$ is carboxyl, carboxymethyl or hydroxymethyl;

R$_3$ is C$_{1-6}$alkyl substituted with phenylthio, C$_{3-7}$cycloalkylthio or 5- to 6-membered heteroarylthio; or propargyl substituted with phenyl, C$_{3-7}$cycloalkyl or 5- to 6-membered heteroaryl;

wherein said heteroaryl is having 1 to 4 heteroatoms chosen from nitrogen, oxygen and sulfur; and wherein said phenyl or said heteroaryl is optionally substituted with one or more substituents selected from the group consisting of halogen, hydroxyl, alkyl, alkyloxy, trifluoromethyl, trifluoromethoxy, carboxyl, alkyloxycarbonyl, cyano and amino; and wherein said cycloalkyl is optionally substituted with one or more substituents chosen from halogen and trifluoromethyl; and R$_4$ is C$_{1-6}$alkyl, C$_{2-6}$alkenyl-CH$_2$— or C$_{2-6}$alkynyl-CH$_2$—, C$_{3-8}$cycloalkyl or C$_{3-8}$cycloalkylalkyl; or an isomer, an enantiomer, a diastereoisomer or a mixture thereof, or a pharmaceutically acceptable salt thereof.

2. The compound as set forth in claim 1, wherein R$_{1a}$ is hydroxyl and R$_{1b}$ is hydrogen.

3. The compound as set forth in claim 1, wherein R$_{1a}$ and R$_{1b}$ form an oxo group.

4. The compound as set forth in claim 1, wherein R$_4$ is C$_{1-6}$alkyl.

5. The compound as set forth in claim 1, wherein R$_2$ is carboxyl.

6. The compound as set forth in claim 1, wherein $R_3$ is $C_{1-6}$alkyl substituted with an optionally substituted phenylthio, cycloalkylthio or heteroarylthio.

7. The compound as set forth in claim 6, wherein $R_3$ is ethyl substituted with thienylthio or phenylthio substituted with halogen or cyclohexylthio or cyclopentylthio.

8. The compound as set forth in claim 1, which is selected from the group consisting of:

4-[3-hydroxy-3-(3-chloro-6-methoxyquinolin-4-yl)-propyl]-1-[2-(2,5-difluorophenyl-sulfanyl)ethyl] piperidine-3-carboxylic acid; and 4-[3-hydroxy-3-(3-chloro-6-methoxyquinolin-4-yl)-propyl]-1-[2-(2-thienylsulfanyl)ethyl]piperidine-3-carboxylic acid; or an isomer, an enantiomer, a diastereoisomer or a mixture thereof, or a pharmaceutically acceptable salt thereof.

9. A process for preparing a compound of formula (I) as set forth in claim 1 comprising condensing $R_3$—X with a compound of formula (II):

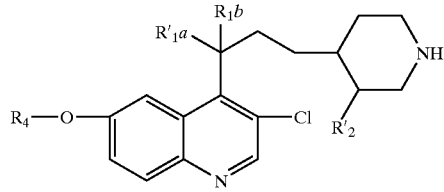

(II)

wherein $R_4$ is as defined in claim 1;

$R'_{1a}$ is hydrogen or hydroxyl; and $R_{1b}$ is hydrogen; or $R'_{1a}$ and $R_{1b}$ form an oxo group; and $R'_2$ is protected carboxyl or carboxymethyl;

to obtain a compound of formula (III):

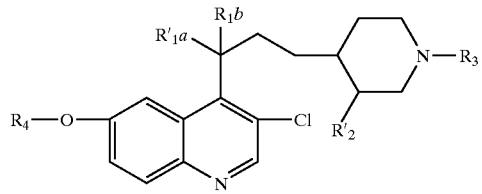

(III)

wherein $R'_{1a}$, $R_{1b}$, $R'_2$, $R_3$ and $R_4$ are as defined above; and optionally treating the compound of formula (III) in which $R'_{1a}$ is hydroxyl and $R_{1b}$ is hydrogen with a halogenating agent; or optionally oxidizing the compound of formula (III) in which $R'_{1a}$ is hydroxyl and $R_{1b}$ is hydrogen to an oxo group; and converting said oxo group to hydroxyimino or alkoxyimino group;

to obtain a compound of formula (IV):

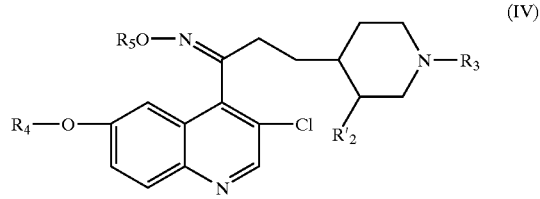

(IV)

wherein $R'_2$, $R_3$ and $R_4$ are as defined above; and $R_5$ is hydrogen or alkyl; and reducing the compound of formula (IV) in which $R_5$ is hydrogen to the corresponding amine; and optionally, alkylating said amine to a monoalkylated or dialkylated amine; or optionally reducing the compound of formula (IV) in which $R_5$ is hydrogen to a hydroxylamine, or reducing the compound of formula (IV) in which $R_5$ is an alkyl to an alkoxyamine; and optionally alkylating said alkoxyamine to obtain the corresponding compound in which $R_{1a}$ is alkylalkoxyamino; and converting $R'_2$ to carboxyl or carboxymethyl; and optionally reducing said carboxyl or protected carboxyl compound to hydroxymethyl compound; and optionally converting said hydroxymethyl compound to carboxymethyl compound; and optionally separating the isomers, and removing the acid-protecting group; and optionally converting said compound to a suitable salt.

10. The process as set forth in claim 9, wherein the compound of formula (II), in which $R'_{1a}$ is hydroxyl, is prepared by oxidation in a basic medium of a corresponding compound for which $R'_{1a}$ and $R_{1b}$ are hydrogen, the amine functional group of the piperidine is protected and $R'_2$ is as defined in claim 9.

11. The process as set forth in claim 9, wherein the compound of formula (II) in which $R'_{1a}$ and $R_{1b}$ form an oxo group is prepared by oxidation of a corresponding compound of formula (II) in which $R'_{1a}$ is a hydroxyl, which is obtained as described in claim 10.

12. The process as set forth in claim 9, wherein the compound of formula (II) in which $R'_2$ represents a protected carboxymethyl, and $R'_{1a}$ and $R_{1b}$ are hydrogen, is prepared by condensing a suitable phosphorous ylide with a compound of formula (IX):

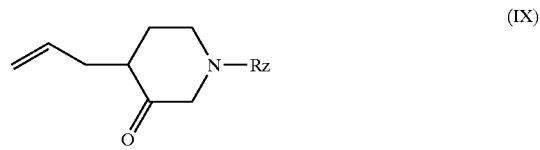

(IX)

wherein Rz is an amino-protecting group; to obtain a compound of formula (VIII):

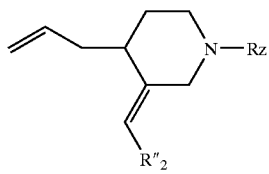
(VIII)

wherein Rz is as defined above and R″₂ is a protected carboxyl; and condensing said compound of formula (VIII) with a compound of formula (VII):

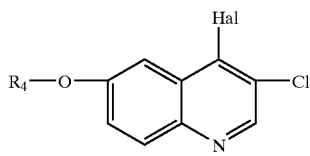
(VII)

wherein R₄ is defined as in claim 1 and Hal represents an iodine or bromine atom;

to obtain a compound of formula (VI):

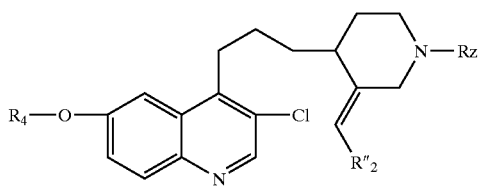
(VI)

wherein R″₂ and Rz are as defined above; and subjecting said compound of formula (VI) to a selective hydrogenation; and optionally deprotecting, where appropriate, the amino group of the piperidine.

13. The process as set forth in claim 12, wherein the compound of formula (II) in which R′₂ is protected carboxyl is prepared by subjecting a compound of formula (II) in which R′₂ is protected carboxymethyl to a reduction to obtain a compound of formula (II) in which R′₂ is hydroxyethyl;

converting said hydroxyethyl compound to a p-toluenesulfonyloxyethyl derivative; and converting said derivative to a vinyl derivative by an elimination reaction; and oxidizing said vinyl derivative and protecting thus obtained carboxyl to obtain compound of formula (II) in which R′₂ is protected carboxyl.

14. The process as set forth in claim 9, wherein the compound of formula (II), in which R′$_{1a}$ and R$_{1b}$ are hydrogen atoms, is prepared by allyation of the keto ester of general formula (XIV):

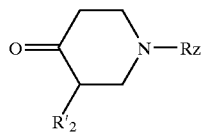
(XIV)

wherein R′₂ is as defined in claim 8 and Rz is as defined in claim 12, to obtain a derivative of general formula (XIII):

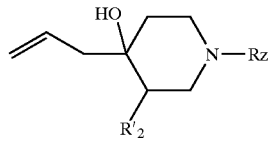
(XIII)

wherein R′₂ and Rz are as defined above, which is reacted with an alkyl oxalyl halide to obtain a derivative of general formula (XII):

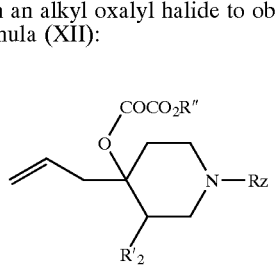
(XII)

wherein R″ represents an alkyl and R′₂ and Rz are as defined above, which is subjected to a deoxygenation reaction, to obtain a derivative of general formula (X):

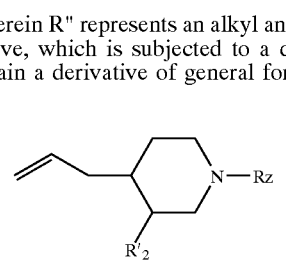
(X)

in which R′₂ and Rz are as defined above, which is condensed with a quinoline derivative of general formula (VII) as defined in claim 10, to obtain a derivative of general formula (XI):

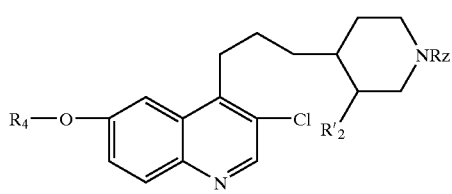
(XI)

and then the amino-protecting radical Rz is removed.

15. The process as set forth in claim 9 wherein the compound formed is 4-[3-hydroxy-3-(3-chloro-6-methoxyquinolin-4-yl)-propyl]-1-[2-(2,5-difluorophenylsulfanyl)ethyl]piperidine-3-carboxylic acid.

16. The process as set forth in claim 9 wherein the compound formed is 4-[3-hydroxy-3-(3-chloro-6-methoxyquinolin-4-yl)-propyl]-1-[2-(2-thienylsulfanyl))ethyl]piperidine-3-carboxylic acid.

17. A pharmaceutical composition comprising therapeutically effective amount of a compound of formula (I) as set forth in claim 1 or a pharmaceutically acceptable salt thereof in combination with a pharmaceutically acceptable carrier.

18. A compound of formula (II):

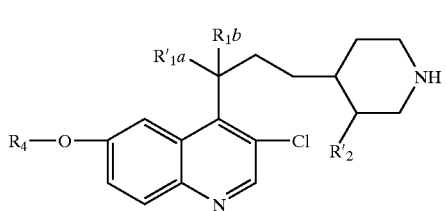

(II)

wherein $R_4$ is as defined in claim 1, either $R'_{1a}$ is hydrogen or hydroxyl and $R_{1b}$ is hydrogen or $R'_{1a}$ and $R_{1b}$ form an oxo group and $R'_2$ is protected carboxyl or carboxymethyl.

19. A compound of formula (A):

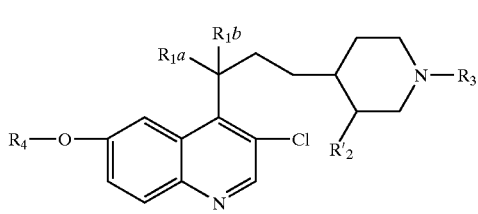

(A)

wherein $R_{1a}$, $R_{1b}$, $R_3$ and $R_4$ are as defined in claim 1 and $R'_2$ is protected carboxyl or carboxymethyl.

20. A compound of formula (IV):

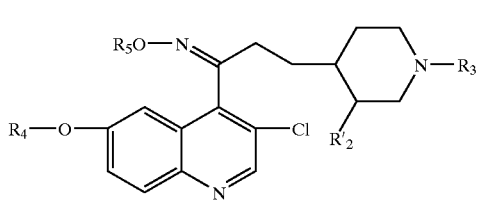

(IV)

wherein $R_3$ and $R_4$ are as defined in claim 1 and $R'_2$ is protected carboxyl or carboxymethyl and $R_5$ is hydrogen or alkyl.

21. A compound of formula (VI):

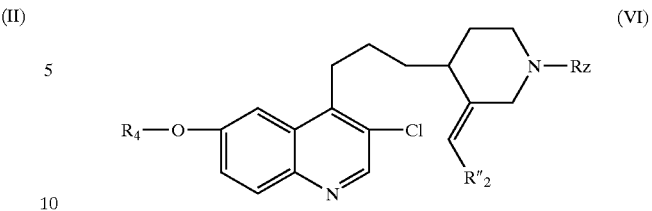

(VI)

wherein $R_4$ is as defined in claim 1 and $R''_2$ is protected carboxyl and Rz is an amino-protecting group.

22. A compound of formula (XI):

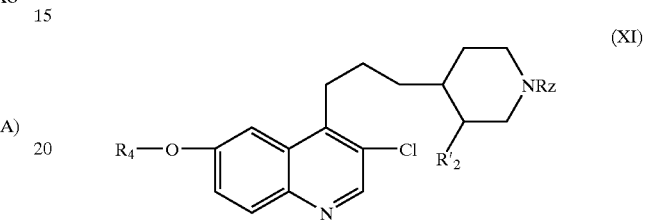

(XI)

wherein $R_4$ is as defined in claim 1, $R'_2$ is protected carboxyl or carboxymethyl and Rz is an amino-protecting group.

23. A method of treatment of a bacterial infection in a patient comprising administering to said patient a therapeutically effective amount of a compound of formula (I) as set forth in claim 1 or a pharmaceutically acceptable salt thereof.

24. The method as set forth in claim 23 wherein said bacterial infection is caused by gram (+) bacteria.

25. The method as set forth in claim 23 wherein said bacterial infection is staphylococcic infection.

26. The method as set forth in claim 23 wherein said staphylococcic infection is selected from the group consisting of staphylococcal septicemias, malignant staphylococcic infections of the face or skin, pyoderma, septic or suppurant wounds, anthrax, phlegmons, erysipelas, acute primary or post-influenza staphylococcic infections, bronchopneumonias and pulmonary suppurations.

27. The method as set forth in claim 23 wherein said bacterial infection is colibacilloses and related infections, proteus infection, klebsiella infection, salmonella infection, and infection caused by gram (−) bacteria.

* * * * *